United States Patent
Libinaki

(10) Patent No.: US 10,188,670 B2
(45) Date of Patent: *Jan. 29, 2019

(54) COMPOSITION

(71) Applicant: Phosphagenics Limited, Clayton, Victoria (AU)

(72) Inventor: Roksan Libinaki, Clayton (AU)

(73) Assignee: Phosphagenics Limited, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,356

(22) Filed: Jan. 6, 2017

(65) Prior Publication Data

US 2017/0112863 A1    Apr. 27, 2017

Related U.S. Application Data

(63) Continuation of application No. 14/004,973, filed as application No. PCT/AU2012/000220 on Mar. 2, 2012, now Pat. No. 9,561,243.

(60) Provisional application No. 61/452,692, filed on Mar. 15, 2011.

(30) Foreign Application Priority Data

Jul. 20, 2011 (AU) ............................... 2011902893

(51) Int. Cl.
| | | |
|---|---|---|
| A61K 31/66 | (2006.01) | |
| A61K 31/665 | (2006.01) | |
| A61K 47/44 | (2017.01) | |
| A61K 9/00 | (2006.01) | |
| A61K 33/04 | (2006.01) | |
| A61K 33/34 | (2006.01) | |
| A61K 33/30 | (2006.01) | |
| A61K 45/06 | (2006.01) | |
| A61K 31/07 | (2006.01) | |
| A61K 31/015 | (2006.01) | |
| A61K 31/355 | (2006.01) | |
| A61K 9/06 | (2006.01) | |
| A23K 20/174 | (2016.01) | |
| A23K 50/10 | (2016.01) | |

(52) U.S. Cl.
CPC .......... *A61K 31/665* (2013.01); *A23K 20/174* (2016.05); *A23K 50/10* (2016.05); *A61K 9/0014* (2013.01); *A61K 9/0019* (2013.01); *A61K 9/0041* (2013.01); *A61K 9/0053* (2013.01); *A61K 9/0095* (2013.01); *A61K 9/06* (2013.01); *A61K 31/015* (2013.01); *A61K 31/07* (2013.01); *A61K 31/355* (2013.01); *A61K 31/66* (2013.01); *A61K 33/04* (2013.01); *A61K 33/30* (2013.01); *A61K 33/34* (2013.01); *A61K 45/06* (2013.01); *A61K 47/44* (2013.01)

(58) Field of Classification Search
CPC .. A61K 9/0014; A61K 9/0019; A61K 9/0041; A61K 9/0053; A61K 9/0095; A61K 9/06; A61K 31/665; A61K 31/015; A61K 31/355; A61K 31/66; A61K 33/30; A61K 33/04; A61K 33/34; A61K 45/06; A61K 47/44; A23K 20/174; A23K 50/10

See application file for complete search history.

(56) References Cited

U.S. PATENT DOCUMENTS

| | | |
|---|---|---|
| 2,407,823 A | 9/1946 | Fieser |
| 2,457,932 A | 1/1949 | Solmssen et al. |
| 2,667,479 A | 1/1954 | Hoffman et al. |
| 2,913,477 A | 11/1959 | Hirschmann |
| 3,127,434 A | 3/1964 | Andrews |
| 3,212,901 A | 10/1965 | Robeson |
| 3,607,765 A | 9/1971 | Wixon |
| 4,075,333 A | 2/1978 | Josse |
| 4,141,938 A | 2/1979 | Klose |
| 4,299,906 A | 11/1981 | Liu |
| 4,369,172 A | 1/1983 | Schor et al. |
| 4,444,755 A | 4/1984 | Horrobin |
| 4,603,142 A | 7/1986 | Burger et al. |
| 4,654,373 A | 3/1987 | Bertelli |
| 4,684,520 A | 8/1987 | Bertelli |
| 4,686,211 A | 8/1987 | Hara et al. |
| 4,874,883 A | 10/1989 | Uphues et al. |
| 4,952,495 A | 8/1990 | Belly et al. |
| 4,977,282 A | 12/1990 | Baldwin et al. |
| 5,041,434 A | 8/1991 | Lubkin |
| 5,053,222 A | 10/1991 | Takasu et al. |
| 5,091,848 A | 2/1992 | Kojima |
| 5,094,848 A | 3/1992 | Brixner |
| 5,114,957 A | 5/1992 | Hendler et al. |

(Continued)

FOREIGN PATENT DOCUMENTS

| | | |
|---|---|---|
| CA | 1337992 | 1/1996 |
| CA | 2426852 | 5/2002 |

(Continued)

OTHER PUBLICATIONS

U.S. Appl. No. 15/218,719, Gavin et al., filed Jul. 25, 2016.
U.S. Appl. No. 15/261,455, Gavin et al., filed Sep. 9, 2016.
Blom, J.H. et al., "Reproductive success of female rainbow trout (*Oncorhynchus mykiss*) in response to graded dietary ascorbyl monophosphate levels," Biol. of Reproduction (1995) 52:1073-1080.
Blum, A. et al., "Clinical and inflammatory effects of dietary L-arginine in patients with intractable angina pectoris," Amer. J. Cardiol. (1999) 1488-1489.

(Continued)

*Primary Examiner* — Blessing M Fubara
(74) *Attorney, Agent, or Firm* — Michael Best & Friedrich LLP

(57) ABSTRACT

Compositions and formulations comprising a non-neutralized tocol phosphate and a vitamin A compound, which are suitable for the treatment of inflammation and/or infection in breast or udder tissue, more particularly in a mammary gland, reducing the somatic cell count in a lactating subject and supplementing vitamin E levels in a subject.

19 Claims, 2 Drawing Sheets

(56) References Cited

U.S. PATENT DOCUMENTS

| | | |
|---|---|---|
| 5,138,084 A | 8/1992 | Casagrande et al. |
| 5,173,304 A | 12/1992 | Lohner et al. |
| 5,334,378 A | 8/1994 | Mitani et al. |
| 5,374,645 A | 12/1994 | Kurihara-Bergstrom et al. |
| 5,387,579 A | 2/1995 | Meybeck et al. |
| 5,446,070 A | 8/1995 | Mantelle |
| 5,474,891 A | 12/1995 | Murphy |
| 5,474,991 A | 12/1995 | Ogata et al. |
| 5,554,781 A | 9/1996 | Reierson |
| 5,570,504 A | 11/1996 | Distefano et al. |
| 5,583,105 A | 12/1996 | Kovacs et al. |
| 5,589,504 A | 12/1996 | Dannenberg et al. |
| 5,603,949 A | 2/1997 | Meybeck et al. |
| 5,607,921 A | 3/1997 | Bernard et al. |
| 5,643,597 A | 7/1997 | Meybeck et al. |
| 5,656,618 A | 8/1997 | Meybeck et al. |
| 5,656,672 A | 8/1997 | Collin et al. |
| 5,741,518 A | 4/1998 | Ribier et al. |
| 5,759,526 A | 6/1998 | Simonnet et al. |
| 5,776,915 A | 7/1998 | Peterson et al. |
| 5,780,504 A | 7/1998 | Ptchelintsev |
| 5,804,168 A | 9/1998 | Murad |
| 5,804,216 A | 9/1998 | Terren et al. |
| 5,807,542 A | 9/1998 | Challis et al. |
| 5,807,845 A | 9/1998 | Ogata et al. |
| 5,885,595 A | 3/1999 | Corey et al. |
| 5,906,811 A | 5/1999 | Hersh |
| 5,908,846 A | 6/1999 | Bundgaard et al. |
| 5,916,915 A | 6/1999 | Hong et al. |
| 5,928,631 A | 7/1999 | Lucas et al. |
| 5,952,361 A | 9/1999 | Dias Nahoum |
| 5,952,373 A | 9/1999 | Lanzendorfer et al. |
| 5,965,750 A | 10/1999 | Oonishi et al. |
| 5,981,474 A | 11/1999 | Manning et al. |
| 5,985,856 A | 11/1999 | Stella et al. |
| 6,022,867 A | 2/2000 | Ito et al. |
| 6,028,105 A | 2/2000 | Nigra |
| 6,046,181 A | 4/2000 | Oonishi et al. |
| 6,048,891 A | 4/2000 | Wechter |
| 6,096,326 A | 8/2000 | Wikholm |
| 6,121,249 A | 9/2000 | Weissman et al. |
| 6,143,770 A | 11/2000 | Lane et al. |
| 6,184,247 B1 | 2/2001 | Schneider |
| 6,231,885 B1 | 5/2001 | Carrara |
| 6,248,758 B1 | 6/2001 | Klokkers et al. |
| 6,248,779 B1 | 6/2001 | Shimizu et al. |
| 6,361,800 B1 | 3/2002 | Cooper et al. |
| 6,384,043 B1 | 5/2002 | Peyman et al. |
| 6,403,811 B1 | 6/2002 | West |
| 6,417,223 B1 | 7/2002 | Sanders et al. |
| 6,423,742 B1 | 7/2002 | Larson |
| 6,444,220 B2 | 9/2002 | Wiley |
| 6,444,234 B1 | 9/2002 | Kirby et al. |
| 6,479,540 B1 | 11/2002 | Constantinides et al. |
| 6,485,950 B1 | 11/2002 | Kumar et al. |
| 6,503,545 B1 | 1/2003 | Perlman et al. |
| 6,579,995 B1 | 6/2003 | West |
| 6,599,933 B2 | 7/2003 | Takada et al. |
| 6,641,847 B1 | 11/2003 | Nawar |
| 6,645,998 B2 | 11/2003 | Sanders et al. |
| 6,703,384 B2 | 3/2004 | Sanders et al. |
| 6,727,280 B2 | 4/2004 | Paiepu et al. |
| 6,770,672 B1 | 8/2004 | Sanders et al. |
| 6,887,648 B2 | 5/2005 | Pavelchek et al. |
| 7,074,825 B2 | 7/2006 | Mo et al. |
| 7,179,486 B1 | 2/2007 | Mulye |
| 7,648,710 B2 | 1/2010 | West |
| 8,008,345 B2 | 8/2011 | West et al. |
| 8,529,947 B2 | 9/2013 | West et al. |
| 8,652,511 B2 | 2/2014 | Cottrell et al. |
| 9,314,527 B2 | 4/2016 | Cottrell et al. |
| 2001/0006659 A1 | 7/2001 | Koike et al. |
| 2001/0044462 A1 | 11/2001 | Hensley et al. |
| 2002/0045765 A1 | 4/2002 | Kim et al. |
| 2002/0127198 A1 | 9/2002 | Rothbard et al. |
| 2002/0131994 A1 | 9/2002 | Schur et al. |
| 2002/0132845 A1 | 9/2002 | Miller et al. |
| 2002/0151467 A1 | 10/2002 | Leung |
| 2003/0035812 A1 | 2/2003 | Ito et al. |
| 2003/0109575 A1 | 6/2003 | Lambert et al. |
| 2003/0157326 A1 | 8/2003 | Vaghefi et al. |
| 2003/0206972 A1 | 11/2003 | Babish et al. |
| 2003/0220301 A1 | 11/2003 | Lal et al. |
| 2004/0052745 A1 | 3/2004 | Bernard et al. |
| 2004/0052754 A1 | 3/2004 | West et al. |
| 2004/0062817 A1 | 4/2004 | Peshoff |
| 2004/0067890 A1 | 4/2004 | Gupta |
| 2004/0097431 A1 | 5/2004 | Sanders et al. |
| 2004/0097472 A1 | 5/2004 | West et al. |
| 2004/0102385 A1 | 5/2004 | Ames et al. |
| 2004/0131569 A1 | 7/2004 | Schneider et al. |
| 2004/0167081 A1 | 8/2004 | Abbruzzese et al. |
| 2004/0204343 A1 | 10/2004 | Fishman |
| 2004/0234602 A1 | 11/2004 | Fischer et al. |
| 2004/0235938 A1 | 11/2004 | Sanders et al. |
| 2004/0241225 A1 | 12/2004 | West |
| 2005/0009787 A1 | 1/2005 | West et al. |
| 2005/0089495 A1 | 4/2005 | West |
| 2005/0134664 A1 | 6/2005 | Pavlin |
| 2005/0142174 A1 | 6/2005 | Assmus et al. |
| 2005/0220733 A1 | 10/2005 | Tsuzuki et al. |
| 2006/0120979 A1 | 6/2006 | Rubin |
| 2006/0228395 A1 | 10/2006 | Lamb et al. |
| 2006/0241085 A1 | 10/2006 | West et al. |
| 2006/0257459 A1 | 11/2006 | West et al. |
| 2006/0281715 A1 | 12/2006 | West |
| 2006/0281716 A1 | 12/2006 | West et al. |
| 2007/0042999 A1 | 2/2007 | West et al. |
| 2007/0110739 A1 | 5/2007 | Logsdon |
| 2007/0135390 A1 | 6/2007 | West et al. |
| 2007/0141133 A1 | 6/2007 | Wang et al. |
| 2007/0224253 A1 | 9/2007 | Franklin |
| 2008/0233178 A1 | 9/2008 | Reidenberg et al. |
| 2008/0254073 A1 | 10/2008 | Chi |
| 2008/0299100 A1 | 12/2008 | Hsia et al. |
| 2009/0004166 A1 | 1/2009 | West et al. |
| 2009/0005348 A1 | 1/2009 | Ogru et al. |
| 2009/0036354 A1 | 2/2009 | Gavin et al. |
| 2009/0104258 A1 | 4/2009 | Dumas et al. |
| 2009/0186856 A1 | 7/2009 | West et al. |
| 2009/0233881 A1 | 9/2009 | West et al. |
| 2009/0239827 A1 | 9/2009 | Ogru et al. |
| 2009/0274677 A1 | 11/2009 | Isaacs et al. |
| 2009/0319191 A1* | 12/2009 | Rivas .............. G01N 33/5091 702/19 |
| 2009/0325953 A1* | 12/2009 | Sahoo .............. C07D 519/00 514/234.2 |
| 2009/0325974 A1* | 12/2009 | Eggenweiler ........ C07D 231/12 514/252.05 |
| 2010/0076094 A1 | 3/2010 | West et al. |
| 2010/0222305 A1 | 9/2010 | West et al. |
| 2010/0261670 A1 | 10/2010 | West et al. |
| 2011/0003774 A1 | 1/2011 | West et al. |
| 2012/0202780 A1 | 8/2012 | Gavin et al. |
| 2012/0283233 A1 | 11/2012 | Gavin et al. |
| 2014/0255509 A1 | 9/2014 | Libinaki et al. |
| 2016/0184436 A1 | 6/2016 | Cottrell et al. |

FOREIGN PATENT DOCUMENTS

| | | |
|---|---|---|
| CA | 2426885 | 5/2002 |
| CN | 1600297 | 3/2005 |
| CN | 102079756 | 9/2012 |
| EP | 0171009 | 2/1986 |
| EP | 0324387 | 7/1989 |
| EP | 0338429 | 10/1989 |
| EP | 0430045 | 6/1991 |
| EP | 0430336 | 6/1991 |
| EP | 0436911 | 7/1991 |
| EP | 0565007 | 10/1993 |
| EP | 0574255 | 12/1993 |
| EP | 0612521 | 8/1994 |
| EP | 0617963 | 10/1994 |
| EP | 0641790 | 3/1995 |

(56) References Cited

FOREIGN PATENT DOCUMENTS

| | | |
|---|---|---|
| EP | 0643969 | 3/1995 |
| EP | 0650721 | 5/1995 |
| EP | 0661053 | 7/1995 |
| EP | 0669132 | 8/1995 |
| EP | 0669437 | 8/1995 |
| EP | 0674904 | 10/1995 |
| EP | 0679399 | 11/1995 |
| EP | 0680760 | 11/1995 |
| EP | 0681840 | 11/1995 |
| EP | 0684043 | 12/1995 |
| EP | 0699440 | 3/1996 |
| EP | 0826365 | 3/1998 |
| EP | 0 845 216 A1 * | 6/1998 |
| EP | 0845216 | 6/1998 |
| EP | 0699437 | 12/1998 |
| EP | 0965328 | 12/1999 |
| EP | 1000541 | 5/2000 |
| EP | 1023897 | 8/2000 |
| EP | 1053749 | 11/2000 |
| EP | 1264595 | 12/2002 |
| EP | 1470817 | 10/2004 |
| EP | 1783209 | 5/2007 |
| FR | 2777179 | 10/1999 |
| GB | 778142 | 7/1957 |
| GB | 1121683 | 7/1968 |
| GB | 2227662 | 8/1990 |
| JP | 50022535 | 3/1975 |
| JP | 52039013 | 3/1977 |
| JP | 53015381 | 2/1978 |
| JP | 58180410 | 10/1983 |
| JP | 59044375 | 3/1984 |
| JP | 59157091 | 9/1984 |
| JP | 60197621 | 10/1985 |
| JP | 61086940 | 5/1986 |
| JP | 61091137 | 5/1986 |
| JP | 61176535 | 8/1986 |
| JP | 61233631 | 10/1986 |
| JP | 62195393 | 8/1987 |
| JP | 63093791 | 4/1988 |
| JP | 63139972 | 6/1988 |
| JP | 1228920 | 9/1989 |
| JP | 1274830 | 11/1989 |
| JP | 03-072426 | 3/1991 |
| JP | 03-120230 | 5/1991 |
| JP | 4208209 | 7/1992 |
| JP | 4270212 | 9/1992 |
| JP | 05-000946 | 1/1993 |
| JP | 5132700 | 5/1993 |
| JP | 5201858 | 8/1993 |
| JP | 6048962 | 2/1994 |
| JP | 6056699 | 3/1994 |
| JP | 6078214 | 10/1994 |
| JP | 7011291 | 1/1995 |
| JP | 7207298 | 8/1995 |
| JP | 7278587 | 10/1995 |
| JP | 7316170 | 12/1995 |
| JP | 8073338 | 3/1996 |
| JP | 8193089 | 7/1996 |
| JP | 08-231564 | 9/1996 |
| JP | 8311085 | 11/1996 |
| JP | 8311489 | 11/1996 |
| JP | 8325594 | 12/1996 |
| JP | 9044375 | 2/1997 |
| JP | 9309813 | 12/1997 |
| JP | 10045783 | 2/1998 |
| JP | 10155429 | 6/1998 |
| JP | 10509451 | 9/1998 |
| JP | 10511677 | 11/1998 |
| JP | 11043436 | 2/1999 |
| JP | 11506419 | 6/1999 |
| JP | 11199424 | 7/1999 |
| JP | 11199465 | 7/1999 |
| JP | 2000198701 | 7/2000 |
| JP | 2001169731 | 6/2001 |
| JP | 2001247585 | 9/2001 |
| JP | 2002080475 | 3/2002 |
| JP | 2002088091 | 3/2002 |
| JP | 2003128531 | 5/2003 |
| JP | 2003171313 | 6/2003 |
| JP | 2006143660 | 6/2008 |
| NZ | 244549 | 7/1994 |
| RU | 2296743 | 4/2007 |
| RU | 2302857 | 7/2007 |
| RU | 2373957 | 11/2009 |
| SU | 925961 | 5/1982 |
| UA | 29476 | 11/2000 |
| WO | WO 91/17987 | 11/1991 |
| WO | WO 92/03122 | 3/1992 |
| WO | WO 92/07544 | 5/1992 |
| WO | WO 92/08459 | 5/1992 |
| WO | WO 92/15289 | 9/1992 |
| WO | WO 93/02661 | 2/1993 |
| WO | WO 93/09768 | 5/1993 |
| WO | WO 93/15731 | 8/1993 |
| WO | WO 93/24131 | 12/1993 |
| WO | WO 95/31217 | 11/1995 |
| WO | WO 95/34303 | 12/1995 |
| WO | WO 96/17852 | 6/1996 |
| WO | WO 96/20715 | 7/1996 |
| WO | WO 96/21440 | 7/1996 |
| WO | WO 96/29336 | 9/1996 |
| WO | WO 96/37196 | 11/1996 |
| WO | WO 97/02803 | 1/1997 |
| WO | WO 97/14705 | 4/1997 |
| WO | WO 97/35591 | 10/1997 |
| WO | WO 99/35242 | 7/1999 |
| WO | WO 99/58555 | 11/1999 |
| WO | WO 00/08033 | 2/2000 |
| WO | WO 00/16772 | 3/2000 |
| WO | WO 00/30620 | 6/2000 |
| WO | WO 00/43380 | 7/2000 |
| WO | WO 00/44237 | 8/2000 |
| WO | WO 00/44375 | 8/2000 |
| WO | WO 00/53728 | 9/2000 |
| WO | WO 00/57876 | 10/2000 |
| WO | WO 00/59475 | 10/2000 |
| WO | WO 00/69865 | 11/2000 |
| WO | WO 00/71094 | 11/2000 |
| WO | WO 00/71125 | 11/2000 |
| WO | WO 00/74684 | 12/2000 |
| WO | WO 01/13901 | 3/2001 |
| WO | WO 01/19372 | 3/2001 |
| WO | WO 01/22937 | 4/2001 |
| WO | WO 01/35883 | 5/2001 |
| WO | WO 01/35998 | 5/2001 |
| WO | WO 01/46204 | 6/2001 |
| WO | WO 01/54674 | 8/2001 |
| WO | WO 01/58889 | 8/2001 |
| WO | WO 01/072300 | 10/2001 |
| WO | 02/02385 | 1/2002 |
| WO | WO 02/13810 | 2/2002 |
| WO | WO 02/26238 | 4/2002 |
| WO | WO 02/36736 | 5/2002 |
| WO | WO 02/39996 | 5/2002 |
| WO | WO 02/40033 | 5/2002 |
| WO | WO 02/40034 | 5/2002 |
| WO | 2002/096217 | 12/2002 |
| WO | WO 03/011303 | 2/2003 |
| WO | WO 03/013550 | 2/2003 |
| WO | WO 03/024429 | 3/2003 |
| WO | WO 03/024430 | 3/2003 |
| WO | WO 03/026673 | 4/2003 |
| WO | WO 03/039461 | 5/2003 |
| WO | WO 03/043570 | 5/2003 |
| WO | WO 03/049774 | 6/2003 |
| WO | WO 03/053407 | 7/2003 |
| WO | WO 03/068209 | 8/2003 |
| WO | WO 03/097714 | 11/2003 |
| WO | WO 03/101480 | 12/2003 |
| WO | WO 2004/014432 | 2/2004 |
| WO | WO 2004/060315 | 7/2004 |
| WO | WO 2004/064831 | 8/2004 |
| WO | WO 2004/091636 | 10/2004 |
| WO | WO 2004/092186 | 10/2004 |

(56) References Cited

FOREIGN PATENT DOCUMENTS

| WO | WO 2004/092187 | | 10/2004 |
|----|----|----|----|
| WO | WO 2005/023282 | | 3/2005 |
| WO | WO 2005/084678 | | 9/2005 |
| WO | WO 2006/012692 | | 2/2006 |
| WO | WO 2006/041506 | | 4/2006 |
| WO | WO 2006/092024 | | 9/2006 |
| WO | WO 2006/092025 | | 9/2006 |
| WO | WO 2006/133506 | | 12/2006 |
| WO | WO 2007/070981 | | 6/2007 |
| WO | WO 2007/075883 | | 7/2007 |
| WO | WO 2008/034178 | | 3/2008 |
| WO | WO 2009/146443 | | 12/2009 |
| WO | WO 2011/094814 | | 8/2011 |
| WO | WO 2011094814 A1 | * | 8/2011 |
| WO | 2013/066400 | | 5/2013 |

OTHER PUBLICATIONS

Brandt, M., "Steroid hormone biosynthesis," (2002) printed from http://www.rose_hulman.edu/~brandt/Chem430/Steroids.pdf on Nov. 20, 2010 (7 pages).

Cevc, G. "Transdermal drug delivery of insulin with ultradeformable carriers," Clin. Pharmacokinet. (2003) 42(5):461-474.

Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.

Database WPI—Week Aug. 2011, Thomson Scientific, London, GB, AN 2010-N41794 XP002727982 & CN101837 (2010).

De Wolfe, F.A. et al., "Ligand-binding proteins: their potential for application in systems for controlled delivery and uptake of ligands," Pharmacol. Rev. (2000) 52(2):207-236.

Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.

Devaraj, S. et al., "Modulation of monocyte-macrophage function with alpha-tocopherol: implications for atherosclerosis," Nat. Rev. (2002) 60(1):8-14.

Aberg, F. et al., "Distribution and redox state of ubiquinones in rat and human tissues," Arch. Biochem. Biophys. (1992) 295(2):230-234.

Advantages of Liposomal Delivery Systems for Anthracyclines, Semin. Oncol., 2004, 6 Suppl 13, 5-15.

Almeida, M.E.M. et al., "Evaluation of soybean oil deodorization distillate for Vitamin E recovery," Arq. Biol. Tecnol. (1994) 37(4):1003-1011.

Anslyn, E.V. et al., Modern Physical Organic Chemistry. Chapter 3: Solutions and Non-Covalent Binding Forces. University Science Books. (2006) see p. 146.

Barrett, C.W. et al., "The effect of particle size and vehicle on the percutaneous absorption of fluocinolone acetonide," Brit. J. Dermatol. (1965) 77:576-578.

Barry ("Novel mechanisms and devices to enable successful transdermal drug delivery." Sciences, 2001; 14:101-114).

Berge et al., "Journal Pharmaceutical Sciences," 66:1-19, 1977.

Bikerman, J.J., "Mechanical destruction of young and old foam films," J. Phys. Chem. (1952) 56:164-165.

Block, L.H., "Chapter 44: Medicated Topicals," in Remington: The Science and Practice of Pharmacy, 20th edition, Edited by Alfonso R. Gennaro, Baltimore, MD, Lippincott, Williams & Wilkins (2000) 836-857.

Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.

Griffin, E. et al., "A link between diabetes and atherosclerosis: glucose regulates expression of CD36 at the level of translation," Nature Med. (2001) 7(7):840-846.

Guo, J. et al., "Transdermal delivery of insulin in mice by using Lecithin vesicles as a carrier," Drug Del. (2000) 7:113-116.

Guthrie et al., "VIIth Asian Conference of Nutrition: Lipid Symposium Proceedings," Journal of Nutrition, 1997, vol. 127, pp. 544s-548s.

Heinrichs, J., "Mastitis prevention: the nutritional approach," Feed Mix, 2008, vol. 16, No. 6, 3 pages.

Heron-Milhavet, L. et al., "Muscle-specific overexpression of CD36 reverses the insulin resistance and diabetes of MKR mice," Endocrinology (2004) 145:4667-4676.

Iimura, N. et al., "Complex formation between cationic surfactants and insoluble drugs," Bull. Chem. Soc. Jpn. (1999) 72:2417-2422.

Imada, I. et al., "Photochemical Reaction of Ubiquinone. IV. Coenzymatic activity of ubiquinone and related compounds," Chem. Pharm. Bull. (1965) 13:136-142.

International Specialty Products,"A Product Guide. Performance enhancing Products for Pharmaceuticals," (2005) 20 pages [retrieved on Jul. 27, 2010 from http://web.archieve.org/web/20060623233652/http://abstracts.aapspharmaceutica.com/ExpoAAPS06/Data/EC/Event/Exhibitors/309/4ecb9a3a-65d0-4c69-a762-c60e099922ee.pdf, published on Jun. 23, 2006 as per Wayback Machine].

Devaraj, S. et la., "Alpha tocopherol decreases CD36 expression in human monocyte-derived macrophages," J. Lipid Res. (2001) 42:521-527.

Ernster, L. et al., "Biochemical, physiological and medical aspects of ubiquinone function," Biochim. Biophys. Acta (1995) 1271:195-204.

Fracalossi, D.M. et al., "Oscars, *Astronotus ocellatus*, have a dietary requirement for vitamin C," J. Nutrition (1998) 128:1745-1751.

Frei, B. et al., "Ubiquinol-10 is an effective lipid-soluble antioxidant at physiological concentrations," Proc. Natl. Acad. Sci. (1990) 87:4879-4883.

Gann, P.H. et al., "Lower prostate cancer risk in men with elevated plasma lycopene levels: results of a prospective analysis," Cancer Res. (1999) 59(6):1225-1230.

Gavin, P. et al., "Transdermal deliver yof various molecules in vivo using alpha-tocopheryl phosphate," Drug Delivery Today 2008) 8(9):34-41.

Gianello, R. et al., "Subchronic oral toxicity study of mixed tocopheryl phosphates in rats," Int'l J. Toxicol. (2007) 26:475-490.

Gianello, R. et al., "α-tocopheryl phosphate: a novel, natural form of vitamin E," Free Radical Biol. Med. (2005) 39:970-976.

Godin, B. et al., "Ethosomes: new prospects in transdermal delivery," Crit. Rev. Thera. Drug Car. Syst. (2003) 20(1):63-102.

Lass, A. et al., "Electron transport-linked ubiquinone-dependent recycling of α-tocopherol inhibits autooxidation of mitochondrial membranes," Arch. Biochem. Biophys. (1998) 352(2):229-236.

Lee, C-F. et al., "Attenuation of UV-induced apoptosis by coenzyme Q10 in human cells harboring large-scale deltion of mitochontrial DNA," Ann. N.Y. Acad. Sci. (2005) 1042:429-438 (Was listed as Sikorska et al. previously).

Lei, B. et al.,. Progress in alpha-tocopherol preparation technology, Xiandai Huagong (1997) 17(7):13-15.

Li et al ("Effect of HPMC and Carbopol on the release and floating properties of gastric floating drug delivery system using factorial design." International Journal of Pharmaceutics, 2003; 253:13-22.).

Libinaki, R. et al., "Evaluation of the safety of mixed tocopheryl phosphates (MTP)-a formulation of α-tocopheryl phosphate plus α-di-tocopheryl phosphate," Food Chem. Toxicol. (2006) 44(7):916-932.

Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.

Madhavi et al., "Enhanced transdermal drug penetration of curcumin via ethosomes," Malaysian Journal of Pharmaceutical Sciences (2013) 11(1):49-58.

Magnusson et al., "Terpenes and ethanol enhance the transdermal permeation of the tripeptide thyrotropin releasing hormone in human epidermis," International Journal of Pharmaceutics 157, 1997, 113-121.

(56) References Cited

OTHER PUBLICATIONS

Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.

Isoda, K. et al., "Metformin inhibits proinflammatory responses and nuclear factor-κB in human vascular wall cells," Arterioscler. Thromb. Vasc. Biol. (2006) 26:611-617.

Jiang, Q. et al., "γ-tocopherol induces apoptosis in androgen-responsive LNCaP prostate cancer cells via caspase-dependent and independent mechanisms," Annals of the New York Academy of Sciences, 2004, vol. 103, pp. 399-400.

Jiang, Q. et al., "γ-tocopherol, the major form of vitamin E in the U.S. diet, deserves more attention," Am. J. Clin. Nutri. (2001) 74(6):714-722.

Kagan, V. et al., "Antioxidant effects of ubiquinones in microsomes and mitochondria are mediated by tocopherol recycling," Biochem. Biophys. Res. Commun. (1990) 169(3):851-857.

Karrer, V.P. et al., "d,l-alpha-tocopherol-phosphorsaure-ester," Zurich, Chemisches Institut der Universitat (1933) p. 1137-1138, in German.

King, M.J. et al., "Transdermal delivery of insulin from a novel biphasic lipid system in diabetic rats," Diab. Tech. Therap. (2002) 4(4):479-488.

Knowler, W.C. et al., "Preventing Non-insulin-dependent diabetes," Diabetes (1995) 44:483-488.

Koh, "Antioxidants in a carotenoid-rich edible oil," Journal of Japan Mibyou System Association, 2003, vol. 9, No. 1, pp. 12-13.

Langsjoen, P.H. et al., "Overview of the use of CoQ10 in cardiovascular diseases," Biofactors (1999) 9:273-284.

Mottu, F. et al., "Organic solvents for pharmaceutical parenterals and embolic liquids: a review of toxicity data," PDA Journal of Pharm. Sci. Tech. (2000) 54(6):456-469.

Mukherjee, S. et al., "Cardioprotection with α-tocopheryl phosphate: amelioration of myocardial ischemia reperfusion injury is linked with its ability to generate a survival signal through Akt activation," Biochim. Biophys. Acta (2008) 1782:498-503.

Munteanu et al., "Modulation of cell proliferation and gene expression by—tocopheryl phosphates: relevance to atherosclerosis and inflamation" Biochemical and Biophysical Research Communications, 2004, vol. 318, pp. 311-316.

Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.

Nakayama, S. et al., "Protective effects of a stable, water-soluble vitamin E on photodamage induced by UVB irradiation in cultured mouse skin," Photomedicine and Photobiology (1998) 20:99-100.

Negis, Y. et al., "Molecular mechanism of alpha-tocopheryl-phospate transport across the cell membrane," Biochem. Biophys. Res. Comm. (2007) 359:348-353.

Negis, Y. et al., "On the existence of cellular tocopheryl phosphate, its synthesis, degradation and cellular roles: a hypothesis," IUBMB Life (2005) 57(1):23-25.

Negis, Y. et al., "The effect of tocopheryl phosphates on atherosclerosis progression in rabbits fed with a high cholesterol diet," Arch. Biochem. Biophys. (2006) 450:63-66.

Octoplus, "Formulation Development of Poorly Soluble Drugs" (www.octoplus.nl) (1999) 2 pages (downloaded Nov. 2008).

Maugard et al., "Synthesis of Water-Soluble Retinol Derivatives by Enzymatic Method," Biotechnol. Prog., 2002, vol. 18, pp. 424-428.

Mellors, A. et al., "The inhibition of mitochondrial peroxidation by ubiquinone and ubiquinol," J. Biol. Chem. (1966) 241(19):4353-4356.

Merck Index, The, "Fludarabine to Fludeoxyglucose F18" pages, Thirteenth Edition, Whitehouse Station, NJ (2001) pp. 729-730.

Merck Index, The, "α-estradiol" Thirteenth Edition, Whitehouse Station, NJ (2001) p. 660.

Min, J. et al., "Effect of apoptosis induced by different vitamin E homologous analogues in human hepatoma cells (HepG2)," J. Hygiene Res. China (2003) 32(4):343-345.

Miyamoto, S. et al., "Synthesis of a novel phosphate ester of a vitamin E derivative and its antioxidative activity," Biosci. Biotech. Biochem. (1998) 62(12):2463-2466.

Morgan, T.M. et al., "Transdermal delivery of estradiol in postmenopausal women with a novel topical aerosol," J. Pharm. Sci. (1998) 87(10):1226-1228.

Morgan, T.M. et al., "Enhanced transdermal delivery of sex hormones in swine with a novel topical aerosol," J. Pharm. Sci. (1998) 87(10):1219-1225.

Mortensen, S.A., "Perspectives on therapy of cardiovascular diseases with coenzyme Q10 (ubiquinone)," Clin. Investig. (1993) 71(Suppl.8):S116-S123.

Rezk, B.M. et al., "The extraordinary antioxidant activity of vitamin E phosphate," Biochim. Biophys. Acta (2004) 1683:16-21.

Ricciarelli, R. et al., "Vitamin E reduces the uptake of oxidized LDL by inhibiting CD36 scavenger receptor expression in cultured aortic smooth muscle cells," Circulation (2000) 102:82-87.

Rosenson et al., "Hypertriglyceridemia is associated with an elevated blood viscosity Rosenson: triglycerides and blood viscosity", Atherosclerosis, 2002, vol. 161, Issue 2, pp. 433-439.

Saikinnno (1991) 149-155, 195-198.

Saishinn (1984) 137-147, 190-201.

Schwenke, D.C. et al., "α-tocopherol protects against diet induced atherosclerosis in New Zealand white rabbits," J. Lipid Res. (2002) 43:1927-1938.

Sevast'ianov, V.I. et al., "Transdermal delivery of insulin," Meditsinskaia Tekhnika (2003) 2:21-24.

Seyama, Y. et al., "Comparative effects of Vitamin K2 and estradiol on experiemental arteriosclerosis with diabetes mellitus," Int. J. Vitam. Nutr. Res. (2000) 70(6):301-304, Abstract only.

Sharma H. et al., "An excerpt from the medical textbook Contemporary Ayurverda," Edinburgh: Churchill Livingston, 1998, 6 pages, Retrieved from Internet on Nov. 1, 2012 <URL: http://www.bsherman.net/freeradicals.htm>.

Ogru, E. et al., "Vitamin E phosphate: an endogenous form of vitamin E," Medimond S.r.l. (2003) 127-132.

Ostrenga, J. et al., "Significance of vehicle composition I: Relationship between topical vehicle composition, skin penetrability, and clinical efficacy," J. Pharm. Sci. (1971) 60(8):1175-1179.

Owens, D.R. et al., "Alternative routes of insulin delivery," Diabet. Med. (2003) 20:886-898.

Parker et al., "Neonatal vitamin K administration and childhood cancer in the North of England: retrospective case-control study," BMJ (1998) 316:189-193.

Pastori et al., "Lycopene in association with α-tocopherol inhibits at physiological concentrations proliferation of prostate carcinoma cells," Biochemical and Biophysical Research Communications, 1998, vol. 250, pp. 582-585.

Potts, R.O. et al., "Predicting skin permeability," Pharm. Res. (1992) 9(5):663-669.

Puratchikody, A. et al., "Reverse phase—high performance liquid chromatographic determination of atorvastatin calcium in solid dosage forms," Pharma. Review (2003) 1(2):79-80, 83—STN File CA, Abstract 139:399976 only.

Reference.com, "What are normal pH levels for the human stomach?" 2016, 1-5.

Rerek, M.E. et al., "Disodium lauriminodipropionate tocopheryl phosphates: a potent new anti-inflammatory," Cosmetics & Toiletries magazine (2003) 118(7):63-67.

Walters et al., "The effects of surfactants on penetration across the skin," Inter. J. Cosmetic Sci. (1993) 15:260-270.

Williams, A.C. et al., "Penetration enhancers," Advanced Drug Delivery Reviews (2004) 56(5):603-618.

Younis et al., "The prevention of type 2 diabetes mellitus: recent advances," Q.J. Med. (2004) 97:451-455.

Zia et al., Pharmaceutical Research, vol. 8, No. 4, 1991.

United States Office Action for U.S. Appl. No. 09/979,436 dated Apr. 4, 2002 (6 pages).

United States Office Action for U.S. Appl. No. 09/979,436 dated Sep. 23, 2002 (6 pages).

(56) References Cited

OTHER PUBLICATIONS

United States Office Action for U.S. Appl. No. 10/416,775 dated Nov. 2, 2005 (10 pages).
United States Office Action for U.S. Appl. No. 10/416,775 dated Jun. 12, 2006 (10 pages).
United States Office Action for U.S. Appl. No. 10/416,775 dated Jul. 12, 2007 (11 pages).
Singh, R.B. et al., "Randomized double-blind placebo-controlled trial of coenzyme Q10 in patients with acute myocardial infarction," Cardiov. Drugs Ther. (1998) 12:347-353.
Sinha, V.R. et al., "Coating polymers for colon specific drug delivery: A comparative in vitro evaluation," Acta. Pharm., 2003, vol. 53, pp. 41-47.
Spears, J.W. et al., "Role of antioxidants and trace elements in health and immunity of transition dairy cows," The Veterinary Journal, 2008, 176:70-76.
Squillante et al, European Journal of Pharmaceutics and Biopharmaceutics 46 (1998) 265-271.
Stedman's Medical Dictionary, "Tocopherol," "Tocotrienol," and "Vitamin K1", 22nd Edition, Williams & Wilkins Co. (1972) p. 1303 and 1400.
Suzuki, T. et al., "The solution behavior and the association structure of long-chain monoalkyl phosphates," Chem. Soc. Japan (1986) 633-640, with English abstract.
Teupser, D. et al., "Alpha-tocopherol down-regulates scavenger receptor activity in macrophages," Atherosclerosis (1999) 144:109-115.
Traber, M.G. et al., "Human plasma vitamin E kinetics demonstrates rapid recycling of plasma RRR-alpha-tocophero," Proc. Natl. Acad. Sci. USA (1994) 91:10005-10008.
Visarius, T. et al., "Inhibition of human prostate cancer cell proliferation: vitamin E and lycopene targeted pathways regulating cell cycle progression," FASEB J. (2004) 18(8):C103.
United States Office Action for U.S. Appl. No. 10/462,480 dated Dec. 1, 2006 (10 pages).
United States Office Action for U.S. Appl. No. 10/462,480 dated Nov. 1, 2007 (10 pages).
United States Office Action for U.S. Appl. No. 10/462,480 dated Feb. 20, 2009 (17 pages).
United States Patent Office Action for U.S. Appl. No. 10/462,480 dated Nov. 27, 2009 (9 pages).
United States Patent Office Action for U.S. Appl. No. 12/768,307 dated Oct. 6, 2011 (13 pages).
United States Patent Office Action for U.S. Appl. No. 12/782,438 dated Aug. 30, 2012 (14 pages).
United States Office Action for U.S. Appl. No. 10/485,196 dated May 29, 2008 (23 pages).
United States Office Action for U.S. Appl. No. 10/485,196 dated Jul. 23, 2009 (9 pages).
United States Patent Office Action for U.S. Appl. No. 10/485,196 dated Jan. 25, 2010 (8 pages).
United States Office Action for U.S. Appl. No. 10/416,775 dated Dec. 17, 2008 (6 pages).
United States Patent Office Action for U.S. Appl. No. 12/628,443 dated Feb. 18, 2011 (15 pages).
United States Patent Office Action for U.S. Appl. No. 12/628,443 dated Aug. 5, 2011 (8 pages).
United States Patent Office Notice of Allowance for U.S. Appl. No. 12/628,443 dated Jan. 12, 2012 (7 pages).
United States Office Action for U.S. Appl. No. 10/416,774 dated Sep. 6, 2007 (9 pages).
United States Office Action for U.S. Appl. No. 10/416,774 dated Jun. 11, 2008 (15 pages).
United States Office Action for U.S. Appl. No. 10/416,774 dated Feb. 17, 2009 (15 pages).
United States Office Action for U.S. Appl. No. 10/416,774 dated Apr. 15, 2009 (14 pages).
United States Patent Office Action for U.S. Appl. No. 10/416,774 dated Dec. 18, 2009 (11 pages).
United States Patent Office Action for U.S. Appl. No. 12/834,553 dated Oct. 7, 2011 (11 pages).
United States Office Action for U.S. Appl. No. 10/551,200 dated Jan. 28, 2009 (11 pages).
United States Office Action for U.S. Appl. No. 10/551,201 dated Jan. 24, 2008 (6 pages).
United States Office Action for U.S. Appl. No. 10/551,203 dated Dec. 6, 2006 (13 pages).
United States Office Action for U.S. Appl. No. 10/551,203 dated Sep. 7, 2007 (13 pages).
United States Office Action for U.S. Appl. No. 10/551,203 dated Apr. 11, 2008 (11 pages).
United States Office Action for U.S. Appl. No. 10/551,203 dated Dec. 19, 2008 (13 pages).
United States Office Action for U.S. Appl. No. 10/551,203 dated Jul. 21, 2009 (21 pages).
United States Patent Office Action for U.S. Appl. No. 12/690,735 dated Sep. 27, 2011 (15 pages).
United States Patent Office Action for U.S. Appl. No. 12/690,735 dated Aug. 2, 2012 (9 pages).
United States Patent Office Action for U.S. Appl. No. 11/572,864 dated Mar. 15, 2012 (15 pages).
United States Patent Office Action for U.S. Appl. No. 11/572,864 dated Nov. 8, 2012 (16 pages).
United States Patent Office Action for U.S. Appl. No. 11/572,864 dated Sep. 16, 2013 (10 pages).
United States Patent Office Action for U.S. Appl. No. 11/572,864 dated Jun. 20, 2014 (11 pages).
United States Patent Office Action for U.S. Appl. No. 11/817,439 dated Nov. 24, 2010 (15 pages).
United States Patent Office Action for U.S. Appl. No. 11/817,439 dated May 11, 2011 (11 pages).
United States Patent Office Action for U.S. Appl. No. 11/817,439 dated Jul. 29, 2011 (2 pages).
United States Patent Office Action for U.S. Appl. No. 11/817,439 dated Nov. 7, 2012 (10 pages).
United States Patent Office Action for U.S. Appl. No. 10/485,196 dated Oct. 29, 2010 (13 pages).
United States Patent Office Notice of Allowance for U.S. Appl. No. 10/485,196 dated Apr. 14, 2011 (7 pages).
United States Office Action for U.S. Appl. No. 10/486,142 dated Mar. 18, 2008 (12 pages).
United States Patent Office Action for U.S. Appl. No. 12/212,803 dated Mar. 12, 2010 (13 pages).
United States Office Action for U.S. Appl. No. 10/487,743 dated Dec. 2, 2005 (22 pages).
United States Office Action for U.S. Appl. No. 10/487,743 dated Jul. 27, 2006 (23 pages).
United States Office Action for U.S. Appl. No. 10/498,684 dated Oct. 2, 2008 (21 pages).
United States Office Action for U.S. Appl. No. 10/498,684 dated Jun. 23, 2009 (19 pages).
United States Patent Office Action for U.S. Appl. No. 10/498,684 dated Jul. 7, 2010 (21 pages).
United States Office Action for U.S. Appl. No. 10/524,090 dated Mar. 12, 2008 (12 pages).
United States Patent Office Action for U.S. Appl. No. 10/524,090 dated Mar. 3, 2010 (18 pages).
United States Patent Office Action for U.S. Appl. No. 10/524,090 dated Nov. 23, 2010 (19 pages).
United States Office Action for U.S. Appl. No. 10/542,511 dated Aug. 8, 2007 (19 pages).
United States Office Action for U.S. Appl. No. 10/542,511 dated Mar. 31, 2008 (20 pages).
United States Office Action for U.S. Appl. No. 10/542,511 dated Feb. 5, 2009 (23 pages).
United States Patent Office Action for U.S. Appl. No. 10/542,511 dated Jan. 12, 2010 (13 pages).
United States Patent Office Advisory Action for U.S. Appl. No. 10/542,511 dated May 25, 2010 (3 pages).
United States Patent Office Action for U.S. Appl. No. 12/834,553 dated Apr. 14, 2011 (13 pages).

(56) References Cited

OTHER PUBLICATIONS

United States Patent Office Action for U.S. Appl. No. 13/501,498 dated Jun. 9, 2016 (14 pages).
United States Patent Office Action for U.S. Appl. No. 12/782,560 dated Sep. 1, 2011 (18 pages).
United States Patent Office Action for U.S. Appl. No. 12/782,560 dated May 24, 2012 (22 pages).
United States Patent Office Action for U.S. Appl. No. 13/501,499 dated Sep. 25, 2013 (12 pages).
United States Patent Office Action for U.S. Appl. No. 13/683,698 dated Apr. 24, 2013 (18 pages).
United States Patent Office Final Rejection for U.S. Appl. No. 13/683,698 dated Nov. 14, 2013 (15 pages).
United States Patent Office Action for U.S. Appl. No. 13/683,698 dated Jun. 20, 2014 (17 pages).
United States Patent Office Final Rejection for U.S. Appl. No. 13/683,698 dated Jan. 29, 2015 (17 pages).
United States Patent Office Action for U.S. Appl. No. 13/683,698 dated Sep. 1, 2015 (19 pages).
United States Patent Office Action for U.S. Appl. No. 12/782,564 dated Sep. 1, 2011 (20 pages).
United States Patent Office Action for U.S. Appl. No. 12/782,564 dated May 24, 2012 (25 pages).
United States Patent Office Action for U.S. Appl. No. 13/501,500 dated Dec. 17, 2012 (14 pages).
United States Patent Office Notice of Allowance for U.S. Appl. No. 13/501,500 dated Aug. 21, 2013 (11 pages).
United States Patent Office Action for U.S. Appl. No. 14/086,738 dated May 22, 2014 (14 pages).
United States Patent Office Action for U.S. Appl. No. 14/550,514 dated Apr. 23, 2015 (13 pages).
United States Patent Office Action for U.S. Appl. No. 13/577,124 dated Feb. 14, 2013 (15 pages).
United States Patent Office Final Rejection for U.S. Appl. No. 13/577,124 dated Aug. 2, 2013 (14 pages).
United States Patent Office Action for U.S. Appl. No. 13/577,124 dated Dec. 26, 2014 (9 pages).
United States Patent Office Action for U.S. Appl. No. 11/817,453 dated Oct. 9, 2009 (11 pages).
United States Patent Office Action for U.S. Appl. No. 11/817,453 dated Aug. 2, 2010 (10 pages).
United States Patent Office Action for U.S. Appl. No. 11/817,453 dated Mar. 9, 2011 (12 pages).
United States Patent Office Action for U.S. Appl. No. 11/817,453 dated Oct. 13, 2011 (14 pages).
United States Patent Office Action for U.S. Appl. No. 11/817,453 dated Feb. 21, 2014 (13 pages).
United States Patent Office Action for U.S. Appl. No. 11/917,831 dated Jan. 19, 2011 (10 pages).
United States Patent Office Action for U.S. Appl. No. 11/917,831 dated Oct. 24, 2011 (11 pages).
United States Patent Office Action for U.S. Appl. No. 11/917,831 dated Oct. 3, 2014 (9 pages).
United States Patent Office Notice of Allowance for U.S. Appl. No. 11/917,831 dated Jul. 8, 2015 (7 pages).
United States Patent Office Action for U.S. Appl. No. 12/158,932 dated Aug. 19, 2010 (15 pages).
United States Patent Office Action for U.S. Appl. No. 13/501,494 dated Dec. 18, 2012 (13 pages).
United States Patent Office Final Rejection for U.S. Appl. No. 13/501,494 dated Aug. 22, 2013 (13 pages).
United States Patent Office Action for U.S. Appl. No. 13/501,494 dated Apr. 21, 2014 (19 pages).
United States Patent Office Action for U.S. Appl. No. 13/501,494 dated Nov. 18, 2014 (16 pages).
United States Patent Office Action for U.S. Appl. No. 13/501,498 dated Feb. 21, 2013 (12 pages).
United States Patent Office Final Rejection for U.S. Appl. No. 13/501,498 dated Nov. 14, 2013 (10 pages).
United States Patent Office Action for U.S. Appl. No. 13/501,498 dated Nov. 21, 2014 (9 pages).
United States Patent Office Final Rejection for U.S. Appl. No. 13/501,498 dated Apr. 8, 2015 (16 pages).
United States Patent Office Final Rejection for U.S. Appl. No. 13/577,124 dated Jul. 22, 2015 (11 pages).
United States Patent Office Action for U.S. Appl. No. 13/577,124 dated Jun. 16, 2016 (8 pages).
United States Patent Office Action for U.S. Appl. No. 14/004,973 dated Apr. 9, 2015 (12 pages).
United States Patent Office Final Rejection for U.S. Appl. No. 14/004,973 dated Oct. 20, 2015 (14 pages).
United States Patent Office Action for U.S. Appl. No. 14/004,973 dated Apr. 13, 2016 (13 pages).
United States Patent Office Action for U.S. Appl. No. 13/501,498 dated Dec. 4, 2015 (10 pages).
United States Patent Office Notice of Allowance for U.S. Appl. No. 14/550,514 dated Dec. 10, 2015 (6 pages).
United States Patent Office Action for U.S. Appl. No. 13/501,494 dated Jan. 26, 2016 (20 pages).
United States Patent Office Notice of Allowance for U.S. Appl. No. 14/004,973 dated Sep. 28, 2016 (5 pages).
United States Patent Office Final Rejection for U.S. Appl. No. 13/577,124 dated Nov. 15, 2016 (10 pages).
United States Patent Office Action for U.S. Appl. No. 15/065,510 dated Dec. 12, 2016 (14 pages).
International Search Report, PCT/AU2012/000220, dated Apr. 2, 2012.
Written Opinion for Application No. PCT/AU2012/000220 dated Apr. 2, 2012 (3 pages).
United States Patent Office Action for U.S. Appl. No. 15/261,455 dated Feb. 27, 2017 (12 pages).
Chae, B. J. et al. 'Effects of incremental levels of alpha-tocopherol acetate on performance, nutrient digestibility and meat quality of commercial broilers', Asian Australasian Journal of Animal Sciences. 2006, vol. 19, No. 2, pp. 203-208.
Ghayour-Mobarhan, M. et al., 'α-Tocopheryl Phosphate as a Bioactive Derivative of Vitamin E: A Review of the Literature', Journal of Dietary Supplements. 2014, vol. 12, No. 4, pp. 359-372.
Zingg, J.-M. et al., 'α-Tocopheryl phosphate—An active lipid mediator?', Molecular Nutrition and Food Research. 2010, vol. 54, pp. 679-692.
United States Patent Office Action for U.S. Appl. No. 15/218,719 dated Sep. 25, 2017 (12 pages).
Trommer et al., "Overcoming the Stratum Corneum: The Modulation of Skin Penetration," Skin Pharmacol Physiol, 2006, 19:106-121.
United States Patent Office Action for U.S. Appl. No. 15/261,455 dated Sep. 6, 2017 (10 pages).
Dolfi, S. C. et al., "Inhibitory Effects of Different Forms of Tocopherols, Tocopherol Phosphates, and Tocopherol Quinones on Growth of Colon Cancer Cells," Journal of Agricultural and Food Chemistry, 2013, vol. 61, No. 36, pp. 8533-8540.
International Search Report for Application No. PCT/AU2017/051381 dated Feb. 13, 2018 (7 pages).
International Search Report for Application No. PCT/AU2017/051363 dated Jan. 25, 2018 (8 pages).
United States Patent Office Action for U.S. Appl. No. 15/261,455 dated Mar. 22, 2018 (6 pages).

\* cited by examiner

COMPOSITION

CROSS-REFERENCE TO RELATED APPLICATIONS

This patent application is a continuation of U.S. patent application Ser. No. 14/004,973, filed on 13 Sep. 2013, which is a national stage filing under 35 U.S.C. § 371 of International Application No. PCT/AU2012/000220, filed on 2 Mar. 2012, which claims the benefit of U.S. Provisional Application No. 61/452,692, filed 15 Mar. 2011, and foreign priority to Australian Patent Application No. 2011902893, filed on 20 Jul. 2011. Priority to each application is hereby claimed.

TECHNICAL FIELD

The present invention relates to new compositions suitable for the treatment of inflammation and/or infection in breast or udder tissue, more particularly in a mammary gland. The inflammation and/or infection in a mammary gland may be mastitis.

BACKGROUND

Mastitis is associated with inflammation and/or infection in breast or udder tissue, more particularly in a mammary gland.

Mastitis is a serious problem in all mammals, including humans and animals.

Mastitis in dairy cattle, for example, is an economically devastating disease causing immense economic losses in the dairy industry and is the most expensive production disease in dairy herds worldwide. For example, in Australia and New Zealand combined, there are about 6 million cattle producing milk. About 15% of any given herd suffers clinical or sub-clinical mastitis, and therefore, at any given time there are about 900,000 cattle in Australia and New Zealand alone that are suffering from clinical and sub-clinical mastitis. Currently, every case of clinical mastitis costs farmers at least $200.

The sub-clinical or clinical definition of mastitis is defined by the presence of somatic cells in milk. In Australia and other countries, the payment to the farmer for the milk may be somewhat dependent on somatic cell count. For example, at very low somatic cell counts a premium price may be paid for the milk. On the other hand, milk above a threshold somatic cell count of 400,000 cells/ml is not considered fit for human consumption in Europe.

Current treatments for mastitis include long-acting antibiotics, such as ampicillin, cloxacilin, cephalonium and bismuth subnitrate.

With respect to dairy cattle, in addition to the costs of administering the antibiotics, there is also is a withholding period that must elapse before the milk produced by treated subjects can be used for human consumption. This withholding period varies between the types of antibiotics administered, but is typically about 96 hours. This withholding period results in significant losses in productivity for dairy farms.

With respect to humans, antibiotic treatment may affect breastfeeding.

Accordingly, there is a need for improved or alternative treatments for inflammation and/or infection in breast or udder tissue, more particularly in a mammary gland, for use in livestock, but also in other mammals such as humans, and to address the problems caused by mastitis.

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

SUMMARY

The present invention relates to compositions comprising a non-neutralised tocol phosphate and a vitamin A compound. It has been found that the compositions are suitable for the treatment of inflammation and/or infection in breast or udder tissue, more particularly in a mammary gland. The inflammation and/or infection in a mammary gland may be mastitis. It would advantageous if the present invention avoids the need for antibiotic treatments.

Accordingly, a first aspect of the present invention provides a composition comprising a non-neutralised tocol phosphate and a vitamin A compound.

The non-neutralised tocol phosphate may be a non-neutralised tocopheryl phosphate, a non-neutralised tocotrienyl phosphate, or a combination thereof.

The non-neutralised tocol phosphate may be selected from the group consisting of non-neutralised mono-(tocopheryl) phosphate, non-neutralised mono-(tocopheryl) phosphate monosodium salt, non-neutralised mono-(tocopheryl) phosphate disodium salt, non-neutralised mono-(tocopheryl) phosphate monopotassium salt, non-neutralised mono-(tocopheryl) phosphate dipotassium salt, non-neutralised di-(tocopheryl) phosphate, non-neutralised di-(tocopheryl) phosphate monosodium salt, non-neutralised di-(tocopheryl) phosphate monopotassium salt, non-neutralised mono-(tocotrienyl) phosphate, non-neutralised mono-(tocotrienyl) phosphate monosodium salt, non-neutralised mono-(tocotrienyl) phosphate disodium salt, non-neutralised mono-(tocopheryl) phosphate monopotassium salt, non-neutralised mono-(tocotrienyl) phosphate dipotassium salt, non-neutralised di-(tocotrienyl) phosphate, non-neutralised di-(tocotrienyl) phosphate monosodium salt, non-neutralised di-(tocotrienyl) phosphate monopotassium salt, or a combination thereof.

In some embodiments, the non-neutralised tocol phosphate is a combination of a non-neutralised mono-(tocopheryl) phosphate, non-neutralised mono-(tocopheryl) phosphate monosodium salt, non-neutralised mono-(tocopheryl) phosphate disodium salt, non-neutralised mono-(tocopheryl) phosphate monopotassium salt or non-neutralised mono-(tocopheryl) phosphate dipotassium salt and a non-neutralised di-(tocopheryl) phosphate, non-neutralised di-(tocopheryl) phosphate monosodium salt or non-neutralised di-(tocopheryl) phosphate monopotassium salt. In other embodiments, the non-neutralised tocol phosphate is a combination of a non-neutralised mono-(tocotrienyl) phosphate, non-neutralised mono-(tocotrienyl) phosphate monosodium salt, non-neutralised mono-(tocotrienyl) phosphate disodium salt, non-neutralised mono-(tocopheryl) phosphate monopotassium salt or non-neutralised mono-(tocotrienyl) phosphate dipotassium salt and a non-neutralised di-(tocotrienyl) phosphate, non-neutralised di-(tocotrienyl) phosphate monosodium salt or non-neutralised di-(tocotrienyl) phosphate monopotassium salt.

In one embodiment, the combination is a non-neutralised mono-(tocopheryl) phosphate and a non-neutralised di-(tocopheryl) phosphate.

When the composition comprises a combination, the ratio (w/w %) of non-neutralised mono-(tocol) phosphate to non-neutralised di-(tocol) phosphate may be at least 2:1, or about 4:1 to about 1:4, or about 6:4 to about 8:2. In some embodiments, the ratio may be about 2:1, about 6:4, or about 8:2.

The pH of the non-neutralised tocol phosphate may be less than about 4. In some embodiments, the pH of the non-neutralised tocol phosphate is about 2 to about 4, or about 2 to about 3. In particular embodiments, the pH of the non-neutralised tocol phosphate is about 2 or about 3.

The non-neutralised tocol phosphate may comprise from about 0.01% w/w up to about 40% w/w, from about 0.01% w/w up to about 30% w/w, from about 0.01% w/w up to about 20% w/w, from about 0.01% w/w up to about 10% w/w, from about 0.01% w/w up to about 5% w/w, from about 0.1% w/w up to about 5% w/w, from about 0.1% w/w up to about 2.5% w/w, from about 0.1% w/w up to about 0.5% w/w, or about 0.5% w/w, about 1% w/w, about 2% w/w, about 3% w/w, about 5% w/w, about 10% w/w, or about 20% w/w, of the total concentration of the composition.

The vitamin A compound may be selected from the group consisting of vitamin A, a derivative of vitamin A, a metabolite of vitamin A, a precursor of vitamin A, or pro-vitamin A, or a combination thereof.

The vitamin A compound may be a retinoid. The retinoid may be selected from the group consisting of retinol, retinal (retinaldehyde), tretinoin (retinoic acid), isotretinoin, alitretinoin, etretinate and its metabolite acitrein, tazarotene, bexarotene and adapalene. The vitamin A compound may also be a retinyl ester such as retinyl acetate or retinyl palmitate.

In one embodiment, the vitamin A compound is a carotenoid. The carotenoid may be of the xanthophylls class such as lutein and zeaxanthin or the carotene class such as alpha-carotene, beta-carotene, gamma-carotene, beta-cryptoxanthin and lycopene. In a preferred embodiment, the vitamin A compound is beta-carotene.

In some embodiments, the composition may comprise a combination of a mono-(tocopheryl) phosphate and a di-(tocopheryl) phosphate, and beta-carotene.

The ratio (w/w %) of non-neutralised tocol phosphate to vitamin A compound may be from about 0.01:1 to about 100:1, from about 0.01:1 to about 5:1, from about 0.05:1 to about 2:1, from about 1:1 to about 5:1, from about 10:1 to about 60:1, or from about 30:1 to about 50:1. In some embodiments, the ratio may be about 0.05:1, about 0.1:1, about 1:1, about 5:1, about 10:1, about 25:1, or about 40:1.

The composition may optionally comprise a delivery vehicle. Accordingly, a second aspect of the present invention provides a formulation comprising the composition as defined above and a delivery vehicle. In a preferred embodiment, the delivery vehicle is a hydrophobic delivery vehicle. The hydrophobic delivery vehicle may be a solid or a liquid. The hydrophobic delivery vehicle may be an oil or a wax. Preferably, the hydrophobic delivery vehicle is an oil such as olive oil.

The delivery vehicle may be present in an amount of at least about 60.0% w/w, at least about 80.0% w/w, at least about 90% w/w, at least about 99.0% w/w, or at least about 99.5% w/w, of the total concentration of the formulation. In some embodiments, the delivery vehicle is present in an amount of about 60.0% w/w, about 80.0% w/w, about 90% w/w, about 98% w/w, about 99% w/w, or about 99.5% w/w, of the total concentration of the formulation.

The compositions and the formulations of the present invention may optionally comprise a nutrient compound. The nutrient compound may be selected from the group consisting of coenzyme Q10 (or ubiquinone); ubiquinol; fat-soluble vitamins such as vitamin D compounds (e.g. D2, D3 and their derivatives), vitamin E compounds ($\alpha$, $\beta$, $\gamma$, $\delta$-tocopherols, or, $\alpha$, $\beta$, $\gamma$, $\delta$-tocotrienols), vitamin K compounds (e.g. K1, K2, K3 and their derivatives); folic acid; vitamin B compounds (e.g. B1, B2, B3, B6, and B12); vitamin C; vitamin P; vitamin F; lutein; zeaxanthin; cysteine; flavonoids (e.g. catechins, reserveratrol, proanthocyanidins); isoflavones (e.g. genistein and daidzein); bilberry; *ginkgo biloba*; grape seed extract; phytonutrients (e.g. lycopene, lutein and seaxanthin); alpha lipoic acid; bilberry; bioflavinoids; unsaturated fatty acids (e.g. linoleic acid, conjugated linoleic acid, linolenic acid, omega-3 fatty acids such as docosahexaenoic acid (DHA) and eicosapentaeonic acid (EPA) and their glycerol-esters); calcium; phosphorus; magnesium; fluorine; phosphorus; sulfur; sodium; potassium; chloride; calcium; iodine; cobalt; copper; iron; manganese; molybdenum; selenium; zinc; chromium; cadmium; fluorine; nickel; silicon; tin; vanadium; niacin; and combinations thereof.

The compositions and the formulations of the present invention may be prepared by a variety of techniques. Accordingly, a third aspect of the present invention provides methods for preparing the composition and the formulation as defined above.

One method of preparing the composition defined above comprises the steps of mixing a non-neutralised tocol phosphate and a vitamin A compound, in suitable quantities, with stirring, until complete homogenisation is achieved. Another method of preparing the composition defined above comprises the steps of warming the non-neutralised tocol phosphate to a temperature greater than about 60° C., preferably between about 70° C. and about 80° C., and then adding the vitamin A compound to the non-neutralised tocol phosphate when the non-neutralised tocol phosphate is at a temperature of less than about 40° C., with stirring, until complete homogenisation is achieved. One method for preparing the formulation as defined above comprises the steps of mixing the non-neutralised tocol phosphate and the hydrophobic delivery vehicle, and warming the mixture to a temperature greater than about 60° C., preferably between about 70° C. and about 80° C., and then adding the vitamin A compound to the non-neutralised tocol phosphate when the non-neutralised tocol phosphate is at a temperature of less than about 40° C., with stirring, until complete homogenisation is achieved.

The compositions and the formulations of the present invention are suitable for the treatment of inflammation and/or infection in breast or udder tissue, more particularly in a mammary gland. The inflammation and/or infection in a mammary gland may be mastitis.

Accordingly, a fourth aspect of the present invention provides a method for the treatment of inflammation and/or infection in breast or udder tissue comprising administering the composition or the formulation as defined above to a subject in need thereof. The present invention also provides use of a non-neutralised tocol phosphate and a vitamin A compound for the treatment of inflammation and/or infection in breast or udder tissue. The present invention further provides use of a non-neutralised tocol phosphate and a vitamin A compound in the manufacture of a medicament for the treatment of inflammation and/or infection in breast or udder tissue.

The breast or udder tissue may be a mammary gland.

The inflammation and/or infection in the mammary gland may be mastitis, more particularly puerperal mastitis.

The subject may be a mammal. The mammal may be selected from humans, domestic mammals such as companion animals, working animals, livestock, and zoological/park mammals. Preferably, the subject is a mammal, in particular a female mammal, more particularly a female mammal having developed lactiferous ducts such as a lactating female mammal. Examples of female lactating mammals may be humans or ungulates (even-toed and odd-toed) including cows, goats, sheep, yaks, water buffalos, horses, reindeer, camels, alpacas, bantengs, donkeys, oxen, zebu, moose and bison.

The compositions or the formulations may be administered topically, preferably epicutaneus, or enterally, preferably orally.

Dosage forms for topically or enteral administration are also preferred. The compositions or the formulations may be administered weekly, daily, or multiple times per day.

The dosage level of the non-neutralised tocol phosphate may be about 0.1 to about 20 mg per kg subject body weight per day which can be administered in single or multiple doses. Preferably, the dosage level will be about 0.1 to about 15 mg/kg per day; about 0.1 to about 10 mg/kg per day; more preferably, about 0.1 to about 10 mg/kg per day, about 0.1 to about 5 mg/kg per day, about 0.1 to about 2.5 mg/kg per day, or about 0.1 to about 2 mg/kg per day. A suitable dosage level may be about 0.1 to about 7.5 mg/kg per day. For example, within the above dosage ranges, the dosage may be about 0.1 mg/kg per day, about 0.2 mg/kg per day, about 0.4 mg/kg per day, about 0.6 mg/kg per day, about 0.7 mg/kg per day, about 0.8 mg/kg per day, about 0.9 mg/kg per day, about 1 mg/kg per day, about 1.2 mg/kg per day, about 1.4 mg/kg per day, about 1.5 mg/kg per day, about 1.6 mg/kg per day, about 1.7 mg/kg per day, about 1.8 mg/kg per day, about 1.9 mg/kg per day, about 2 mg/kg per day, about 2.2 mg/kg per day, about 2.5 mg/kg per day, about 3 mg/kg per day, about 5 mg/kg per day, about 7.5 mg/kg per day, or about 10 mg/kg per day.

The dosage level of the vitamin A compound may be about 10 to about 1000 μg per kg subject body weight per day which can be administered in single or multiple doses. Preferably, the dosage level will be about 10 to about 850 μg/kg per day; about 10 to about 800 μg/kg per day; about 10 to about 500 μg/kg per day; or less than about 300 μg/kg per day. More preferably, the dosage level will be about 10 to about 500 μg/kg per day, 10 to about 275 μg/kg per day, 10 to about 250 μg/kg per day, 20 to about 250 μg/kg per day, 25 to about 250 μg/kg per day, 10 to about 200 μg/kg per day, or 50 to about 200 μg/kg per day. A suitable dosage level may be about 10 to about 300 μg/kg per day. For example, within the above dosage ranges, the dosage may be about 10 μg/kg per day, about 20 μg/kg per day, about 40 μg/kg per day, about 50 μg/kg per day, about 60 μg/kg per day, about 70 μg/kg per day, about 75 μg/kg per day, about 80 μg/kg per day, about 85 μg/kg per day, about 90 μg/kg per day, about 95 μg/kg per day, about 100 μg/kg per day, about 125 μg/kg per day, about 150 μg/kg per day, about 155 μg/kg per day, about 160 μg/kg per day, about 165 μg/kg per day, about 170 μg/kg per day, about 175 μg/kg per day, about 180 μg/kg per day, about 190 μg/kg per day, about 200 μg/kg per day, about 225 μg/kg per day, about 250 μg/kg per day, about 300 μg/kg per day, about 400 μg/kg per day, or about 500 μg/kg per day.

A reduction in somatic cell count usually results from the effective treatment of inflammation and/or infection in breast or udder tissue, more particularly a mammary gland. Accordingly, a fifth aspect of the present invention provides a method for reducing the somatic cell count in a lactating subject comprising administering the composition or the formulation as defined above to the lactating subject. The present invention also provides use of a non-neutralised tocol phosphate and a vitamin A compound for reducing the somatic cell count in a lactating subject. The present invention further provides use of a non-neutralised tocol phosphate and a vitamin A compound in the manufacture of a medicament for reducing the somatic cell count in a lactating subject.

The lactating subject may be a female ungulate (even-toed and odd-toed), more particularly an ungulate whose milk is used for commercial purposes including cows, goats, sheep, pigs, yaks, water buffalo, horses, reindeer, camels, alpacas, bantengs, donkeys, oxen, zebu, moose and bison. The lactating subject may also be a lactating human.

Administration of the composition or the formulation to the lactating subject may reduce the somatic cell count by up to 90%, up to 80%, up to 70%, up to 60%, up to 50%, up to 40%, up to 30%, up to 20%, or up to 10%. The reduction may be achieved in 1 week, 2 weeks, 3 weeks, 4 weeks, 5 weeks, or more, with daily or weekly administration of an effective dose of the composition or the formulation to the lactating subject.

A composition or a formulation of the present invention may also supplement vitamin E levels (μmol/L) in a subject. Accordingly, the present invention also provides a method for supplementing vitamin E levels in a subject comprising administering the composition or the formulation as defined above to the subject. The present invention also provides use of a non-neutralised tocol phosphate and a vitamin A compound for supplementing vitamin E levels in a subject. The present invention further provides use of a non-neutralised tocol phosphate and a vitamin A compound in the manufacture of a medicament to supplement vitamin E levels in a subject.

DETAILED DESCRIPTION

The present invention relates to a composition comprising a non-neutralised tocol phosphate and a vitamin A compound.

Non-Neutralised Tocol Phosphate

The term "tocol" includes any of the naturally occurring fat-soluble compounds with vitamin E activity, namely the four tocopherols and the four tocotrienols. The tocopherols and tocotrienols may be natural or synthetic.

The four tocopherols and four tocotrienols occur in alpha, beta, gamma and delta forms, determined by the number and location of methyl groups on the chroman ring. The tocopherol and tocotrienol forms of Vitamin E are shown by Formula (I):

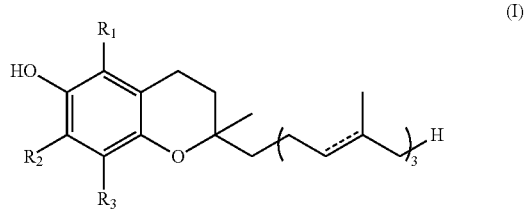

(I)

|  | $R_1$ | $R_2$ | $R_3$ |
| --- | --- | --- | --- |
| α-tocopherol | $CH_3$ | $CH_3$ | $CH_3$ |
| α-tocotrienol | $CH_3$ | $CH_3$ | $CH_3$ |
| β-tocopherol | $CH_3$ | H | $CH_3$ |
| β-tocotrienol | $CH_3$ | H | $CH_3$ |
| γ-tocopherol | H | $CH_3$ | $CH_3$ |

|   | R₁ | R₂ | R₃ |
|---|---|---|---|
| γ-tocotrienol | H | CH₃ | CH₃ |
| δ-tocopherol | H | H | CH₃ |
| δ-tocotrienol | H | H | CH₃ |

The terms "tocopheryl phosphates" and "tocotrienyl phosphates" refer to any one of the tocopherols or tocotrienols, as shown above, where a phosphate group ($PO_4$) is covalently bonded via the oxygen of the hydroxyl group of tocopherol or tocotrienol.

Tocopherol or tocotrienol, in the alpha, beta, gamma or delta form, or a combination thereof, may be phosphorylated by reaction with $P_4O_{10}$. The non-neutralised tocol phosphate is the crude phosphorylation reaction product obtained prior to the neutralisation step.

This crude phosphorylation reaction product may comprise a number of components including both mono- and di-phosphorylated tocol phosphates.

The non-neutralised tocol phosphate may be non-neutralised tocopheryl phosphates, non-neutralised tocotrienyl phosphates, or a combination thereof.

The non-neutralised tocol phosphate may be selected from the group consisting of non-neutralised mono-(tocopheryl) phosphate, non-neutralised mono-(tocopheryl) phosphate monosodium salt, non-neutralised mono-(tocopheryl) phosphate disodium salt, non-neutralised mono-(tocopheryl) phosphate monopotassium salt, non-neutralised mono-(tocopheryl) phosphate dipotassium salt, non-neutralised di-(tocopheryl) phosphate, non-neutralised di-(tocopheryl) phosphate monosodium salt, non-neutralised di-(tocopheryl) phosphate monopotassium salt, non-neutralised mono-(tocotrienyl) phosphate, non-neutralised mono-(tocotrienyl) phosphate monosodium salt, non-neutralised mono-(tocotrienyl) phosphate disodium salt, non-neutralised mono-(tocopheryl) phosphate monopotassium salt, non-neutralised mono-(tocotrienyl) phosphate dipotassium salt, non-neutralised di-(tocotrienyl) phosphate, non-neutralised di-(tocotrienyl) phosphate monosodium salt, non-neutralised di-(tocotrienyl) phosphate monopotassium salt, or a combination thereof.

Other pharmaceutically or veterinary acceptable salts of the tocol phosphate may be used, such as other alkali metal salts. Other pharmaceutically acceptable salts are well known in the art, and include the acceptable salts described in detail in S. M. Berge, et al., J. Pharmaceutical Sciences, 66:1-19, 1977.

In some embodiments, the non-neutralised tocol phosphate is a combination of a non-neutralised neutralised mono-(tocopheryl) phosphate, non-neutralised mono-(tocopheryl) phosphate monosodium salt, non-neutralised mono-(tocopheryl) phosphate disodium salt, non-neutralised mono-(tocopheryl) phosphate monopotassium salt or non-neutralised mono-(tocopheryl) phosphate dipotassium salt and a non-neutralised di-(tocopheryl) phosphate, non-neutralised di-(tocopheryl) phosphate monosodium salt or non-neutralised di-(tocopheryl) phosphate monopotassium salt. In other embodiments, the non-neutralised tocol phosphate is a combination of a non-neutralised mono-(tocotrienyl) phosphate, non-neutralised mono-(tocotrienyl) phosphate monosodium salt, non-neutralised mono-(tocotrienyl) phosphate disodium salt, non-neutralised mono-(tocopheryl) phosphate monopotassium salt or non-neutralised mono-(tocotrienyl) phosphate dipotassium salt and a non-neutralised di-(tocotrienyl) phosphate, non-neutralised di-(tocotrienyl) phosphate monosodium salt or non-neutralised di-(tocotrienyl) phosphate monopotassium salt.

In one embodiment, the combination is a non-neutralised mono-(tocopheryl) phosphate and a non-neutralised di-(tocopheryl) phosphate. It should be noted that a combination of a non-neutralised mono-(tocopheryl) phosphate and a non-neutralised di-(tocopheryl) phosphate may be referred to herein as a non-neutralised tocopheryl phosphate mixture or non-neutralised TPM.

When the composition comprises a combination, the ratio (w/w %) of non-neutralised mono-(tocol) phosphate to non-neutralised di-(tocol) phosphate may be at least 2:1, or about 4:1 to about 1:4, or about 6:4 to about 8:2. In some embodiments, the ratio may be about 2:1, about 6:4, or about 8:2.

The non-neutralised tocol phosphate has a pH of less than about 4 compared to "neutralised" tocol phosphates which have a pH closer to neutral, usually in the range of above 5 to about 7. The pH of the non-neutralised tocol phosphate may be in the range of about 2 to about 4 or about 2 to about 3. Preferably, the pH of the non-neutralised tocol phosphate is about 2 or 3.

The non-neutralised tocol phosphate may comprise from about 0.01% w/w up to about 40% w/w, from about 0.01% w/w up to about 30% w/w, from about 0.01% w/w up to about 20% w/w, from about 0.01% w/w up to about 10% w/w, from about 0.01% w/w up to about 5% w/w, from about 0.1% w/w up to about 5% w/w, from about 0.1% w/w up to about 2.5% w/w, from about 0.1% w/w up to about 0.5% w/w, or about 0.5% w/w, about 1% w/w, about 2% w/w, about 3% w/w, about 5% w/w, about 10% w/w, or about 20% w/w, of the total concentration of the composition.

Vitamin A Compound

The composition of the present invention also comprises a vitamin A compound.

The vitamin A compound should be capable of converting into an active form of vitamin A in the body and/or should be capable of providing, directly or indirectly, a compound having vitamin A activity. The vitamin A compound may be selected from the group consisting of vitamin A, a derivative of vitamin A, a metabolite of vitamin A, a precursor of vitamin A, or pro-vitamin A, or a combination thereof.

Vitamin A has a beta-ionone ring to which an isoprenoid chain is attached, called a retinyl group. Vitamin A is also known as retinol which is a member of the retinoid class.

Retinoids are considered natural or synthetic derivatives of vitamin A. The term encompasses any compound that is structurally similar to retinal (aldehyde), retinol (alcohol), or any other substance that exhibits vitamin A activity. Retinoids may be classified as first, second and third generation retinoids. First generation retinoids include retinol, retinal (retinaldehyde), tretinoin (retinoic acid), isotretinoin and alitretinoin, second generation retinoids include etretinate and its metabolite acitrein, and third generation retinoids include tazarotene, bexarotene and adapalene.

Some examples of vitamin A derivatives capable of providing, directly or indirectly, a compound having vitamin A activity, include derivatives of retinol such as retinyl esters. Examples of retinyl esters include retinyl acetate and retinyl palmitate.

Examples of a metabolite of vitamin A include retinoic acid and retinal.

The vitamin A compound may also be a precursor of vitamin A or pro-vitamin A.

A precursor of vitamin A is any compound that participates in the chemical reaction that produces vitamin A or a vitamin A compound that converts into an active form of vitamin A in the body and/or is capable of providing, directly or indirectly, a compound having vitamin A activity. Provitamin A on the other hand is a substance that can be converted into vitamin A by animal tissues, similar to a prodrug that is metabolised into a drug.

Carotenoids are converted into an active form of vitamin A in the body, and thus have vitamin A activity. There are over 600 known carotenoids, which are split into two classes, xanthophylls (which contain oxygen) such as lutein and zeaxanthin and carotenes (which are purely hydrocarbons, and contain no oxygen) such as alpha-carotene, beta-carotene, gamma-carotene, beta-cryptoxanthin and lycopene.

The amount of vitamin A compound present in the composition may be expressed as a ratio of the amount of non-neutralised tocol phosphate to the amount of vitamin A compound. The ratio (w/w %) of non-neutralised tocol phosphate to vitamin A compound may be from about 0.01:1 to about 100:1, from about 0.01:1 to about 5:1, from about 0.05:1 to about 2:1, from about 1:1 to about 5:1, from about 10:1 to about 60:1, or from about 30:1 to about 50:1. In some embodiments, the ratio may be about 0.05:1, about 0.1:1, about 1:1, about 5:1, about 10:1, about 25:1, or about 40:1.

Formulation

The present invention also relates to a formulation comprising the composition as defined above and a delivery vehicle.

The term "formulation" is intended to refer to the composition with a delivery vehicle and optionally other conventional excipients including encapsulating materials such as a capsule in which the composition is surrounded by the encapsulation material. Any delivery vehicle and conventional excipients must be "pharmaceutically and/or veterinary acceptable" meaning that it is compatible with the components of the composition and is not deleterious to a subject. The formulations of the present invention may contain other therapeutic agents, and may be formulated, for example, by employing conventional solid or liquid vehicles or diluents, as well as pharmaceutical and/or veterinary additives of a type appropriate to the mode of desired administration (for example, excipients, binders, preservatives, stabilisers, flavours and so forth) according to techniques such as those well known in the art of pharmaceutical formulation (see, for example, Remington: *The Science and Practice of Pharmacy*, 21st Ed., 2005, Lippincott Williams & Wilkins).

In a preferred embodiment, the delivery vehicle is a hydrophobic delivery vehicle.

The hydrophobic delivery vehicle may be a solid or a liquid.

Some examples of hydrophobic delivery vehicles which are most suitable for the present invention include, but are not limited to, oils and waxes.

Suitable oil-based hydrophobic delivery vehicles include any oil that is suitable for therapeutic use, such as for example, any edible oil. The oil-based hydrophobic delivery vehicles may be natural or synthetic. The oil-based hydrophobic delivery vehicles should also be compatible with the non-neutralised tocol phosphate and the vitamin A compound.

Preferred oil-based hydrophobic delivery vehicles suitable for use in the composition of the present invention include vegetable oil, fruit oil, seed oil, grain oil, nut oil, or the like. These oils may be saturated or unsaturated. These oils may also be winterised or non-winterised. Examples of suitable oils include canola oil, coconut oil, corn oil, cottonseed oil, olive oil, *Olea europaea* (olive) leaf extract, palm oil, peanut oil, rapeseed oil, safflower oil, sesame oil, soybean oil, sunflower oil, almond oil, cashew oil, hazelnut oil, *macadamia* oil, *Macadamia integrifolia* (*macadamia*) seed oil, mongongo nut oil, pecan oil, pine nut oil, pistachio oil, walnut oil, bottle gourd oil, buffalo gourd oil, pumpkin seed oil, watermelon seed oil, acai oil, blackcurrant seed oil, borage seed oil, evening primrose oil (*Oenothera biennis* oil), amaranth oil, apricot oil, apple seed oil, argan oil, artichoke oil, avocado oil (*Persea gratissima* oil), babassu oil, ben oil, borneo tallow nut oil, cape chestnut oil, cocoa butter, carob pod oil, cocklebur oil, cohune oil, coriander seed oil, dika oil, false flax oil, flax seed oil, grape seed oil (*Vitis vinifera*), hemp oil, kapok seed oil, lallemantia oil, marula oil, meadowfoam seed oil, mustard oil, nutmeg butter, okra seed oil, orange oil, papaya seed oil, perilla seed oil, pequi oil, pine nut oil, poppyseed oil, prune kernel oil, quinoa oil, ramtil oil, rice bran oil (for example, Oryza Satirau Bran Oil), rose hip oil (*Rosa eglanteria* oil), royle oil, sacha inchi oil, sandalwood oil (*Santalum spicatum* oil), tea seed oil, thistle oil, tomato seed oil and wheat germ oil.

Suitable hydrophobic delivery vehicles may also include cetearyl alcohol, cetearyl glucoside, cetearyl olivate, cocoyl proline, dicapryl ether, glycerin, glyceryl linoleate, glyceryl oleate, lactic acid, lecithin, pomegranite sterols, resveratrol and vitamin D3.

Suitable hydrophobic delivery vehicles may also include polyunsaturated oils containing polyunsaturated fatty acids. In one or more embodiments, the unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). In some instances, mixtures of fatty acids or medium chain triglycerides are excluded from the scope of hydrophobic delivery vehicles.

Another class of hydrophobic delivery vehicles is essential oils, which may also be considered therapeutically-active oils if they contain active biologically occurring molecules and exert a therapeutic effect on administration. In the context of the present invention, delivery vehicles that additionally possess therapeutically beneficial properties may be referred to as "therapeutically-active delivery vehicle". If a formulation is made using a therapeutically-active delivery vehicle, then the formulation will include a non-neutralised tocol phosphate and a vitamin A compound as well as the therapeutically-active delivery vehicle. Non-limiting examples of therapeutically-active delivery vehicles include essential oils such as rosehip oil and tea tree oil. Other examples of essential oils are oils of anise, basil, bergamot, camphor, cardamom, carrot, canola, cassia, catnip, cedarwood, citronella, clove, cypress, eucalyptus, frankincense, garlic, ginger, grapefruit, hyssop, jasmine, jojoba, lavender, lavandin, lemon, lime, mandarin, marjoram, myrrh, neroli, nutmeg, orange, peppermint, petitgrain, rosemary, sage, spearmint, star anise, tangerine, thyme vanilla, verbena and white clover.

Another class of therapeutically-active oils includes liquid hydrophobic plant derived oils, which are known to possess therapeutic benefits when applied topically.

Silicone oils also may be used and may be particularly desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)(diphenyl-siloxane) copolymers. Silicone oils may also considered therapeutically-active oil due to their barrier retaining and protective properties.

Hydrophobic liquids selected from the family of organic liquids described as "emollients" is another class of hydrophobic delivery vehicles. Emollients possess a softening or soothing effect, especially when applied to body areas, such as the skin and mucosal surfaces. Examples of suitable emollients include isopropyl myristate, isopropyl palmitate, isopropyl isostearate, diisopropyl adipate, diisopropyl dimerate, maleated soybean oil, octyl palmitate, cetyl lactate, cetyl ricinoleate, tocopheryl acetate, cetyl acetate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, octyl dodecanol, sucrose esters of fatty acids and octyl hydroxystearate.

Suitable hydrophobic delivery vehicles also include pharmaceutically acceptable waxes. An example of a pharmaceutically acceptable wax is beeswax.

It should be noted that, as used in the present specification, the singular forms "a", "an" and "the" include plural aspects unless the context clearly dictates otherwise. Thus, for example, reference to "a hydrophobic delivery vehicle" may refer to a single hydrophobic delivery vehicle, or two or more hydrophobic delivery vehicles, depending on the context, and so forth for other features of the invention.

The delivery vehicle may be present in an amount of at least about 60.0% w/w, at least about 80.0% w/w, at least about 90% w/w, at least about 99.0% w/w, or at least about 99.5% w/w, of the total concentration of the formulation. In some embodiments, the delivery vehicle is present in an amount of about 60.0% w/w, about 80.0% w/w, about 90% w/w, about 98% w/w, about 99% w/w, or about 99.5% w/w, of the total concentration of the formulation.

Nutrient Compound

The composition or the formulation may optionally comprise a nutrient compound.

The term "nutrient compound" encompasses antioxidants, vitamins, minerals and trace elements which are capable of treating inflammation and/or infection in breast or udder tissue of a subject, reducing the somatic cell count in a lactating subject or supplementing vitamin E levels in a subject.

The nutrient compound may be selected from the group consisting of, but is not limited to, coenzyme Q10 (or ubiquinone); ubiquinol; fat-soluble vitamins such as vitamin D compounds (e.g. D2, D3 and their derivatives), vitamin E compounds ($\alpha$, $\beta$, $\gamma$, $\delta$-tocopherols, or $\alpha$, $\beta$, $\gamma$, $\delta$-tocotrienols), vitamin K compounds (e.g. K1, K2, K3 and their derivatives); folic acid; vitamin B compounds (e.g. B1, B2, B3, B6 and B12); vitamin C; vitamin P; vitamin F; lutein; zeaxanthin; cysteine; flavonoids (e.g. catechins, reserveratrol, proanthocyanidins); isoflavones (e.g. genistein and daidzein); bilberry; *ginkgo biloba*; grape seed extract; phytonutrients (e.g. lycopene, lutein and seaxanthin); alpha lipoic acid; bilberry; bioflavinoids; unsaturated fatty acids (e.g. linoleic acid, conjugated linoleic acid, linolenic acid, omega-3 fatty acids such as docosahexaenoic acid (DHA) and eicosapentaenoic acid (EPA) and their glycerol-esters); calcium; phosphorus; magnesium; fluorine; phosphorus; sulfur; sodium; potassium; chloride; calcium; iodine; cobalt; copper; iron; manganese; molybdenum; selenium; zinc; chromium; cadmium; fluorine; nickel; silicon; tin; vanadium; niacin; and combinations thereof.

Excipients

A formulation of the present invention can optionally further comprise one or more excipients. A person skilled in the art of the invention would appreciate suitable excipients that could be included in formulations of the present invention. The choice and amount of excipients will depend on the intended use of formulations, the mode of administration and/or the dosage form.

Examples of suitable excipients include additional solvents such as water, thickeners or gelling agents, surfactants, buffers, emollients, sweeteners, disintegrators, flavours, colours, fragrances, electrolytes, appearance modifiers, film foaming polymers and the like. Suitable sweeteners include sucrose, lactose, glucose, aspartame or saccharin. Suitable disintegrators include corn starch, methylcellulose, polyvinylpyrrolidone, xanthan gum, bentonite, alginic acid or agar. Suitable flavours include peppermint oil, oil of wintergreen, cherry, orange, or raspberry flavouring. Other flavourings may be molasses, salt-licks, and the like, which are particularly suitable for animals. Suitable preservatives include sodium benzoate, methylparaben, propylparaben, and sodium bisulphite. However, it will be appreciated that any excipients, which have been approved for use in pharmaceutical and veterinary products by the regulatory bodies, may be employed in the formulations of the present invention.

Preparation of Compositions and Formulations

The compositions and the formulations of the present invention may be prepared by a variety of techniques.

One method of preparing the composition defined above comprises the steps of mixing a non-neutralised tocol phosphate and a vitamin A compound, in suitable quantities, with stirring, until complete homogenisation is achieved. Another method of preparing the composition defined above comprises the steps of warming the non-neutralised tocol phosphate to a temperature greater than about 60° C., preferably between about 70° C. and about 80° C., and then adding the a vitamin A compound to the non-neutralised tocol phosphate when the non-neutralised tocol phosphate is at a temperature of less than about 40° C., with stirring, until complete homogenisation is achieved. One method for preparing the formulation as defined above comprises the steps of mixing the non-neutralised tocol phosphate and the hydrophobic delivery vehicle, and warming the mixture to a temperature greater than about 60° C., preferably between about 70° C. and about 80° C., and then adding the vitamin A compound to the non-neutralised tocol phosphate when the non-neutralised tocol phosphate is at a temperature of less than about 40° C., with stirring, until complete homogenisation is achieved.

Treatment of Inflammation and/or Infection in Breast or Udder Tissue

The compositions and the formulations of the present invention are suitable for the treatment of inflammation and/or infection in breast or udder tissue, more particularly in a mammary gland. The inflammation and/or infection in a mammary gland may be mastitis.

The "subject" may be mammal including humans and animals. In one embodiment, the mammal is a human, female or male. In other embodiments, the mammal is an animal, in particular of the subclass Theria including the subclasses Metatheria and Eutheria. The mammal may also be a monotreme of the subclass Prototheria. However, it is recognised that these are mammals in which the mammary glands are devoid of teats. This is also the case for a monotremata of the subclass Australospenida which includes the platypus and the echidna.

Under the subclass of Metatheria are the superorders of Ameridelphia and Australidelphia which are inclusive of marsupials such as kangaroos and possums. The subclass of Eutheria is inclusive of placentals. Under the subclass of Eutheria are a number of superorders, which in turn encompass orders. The superorder of Xenarthra includes the orders Cingulata (armadillos) and Pilosa (anteaters and sloths). The superorder of Afrotheria includes the orders Afrosoricida (tenrecs and golden moles), Macroscelidea (elephant shrews), Tubulidentata (aardvarks), Hyracoidea (hyraxes), Proboscidea (elephants) and Sirenia (dugongs and manatees). The superorder of Laurasiatheria includes the orders Soricomorpha (shrews, moles and solenodons), Erinaceomorpha (hedgehogs and relatives), Chiroptera (bats), Pholidota (pangolins), Carnivora (dogs, cats, weasels, bears, seals, and their relatives), Perissodactyla (odd-toed ungulates), Artiodactyla (even-toed ungulates) and Cetacea (whales and dolphins), the latter two orders are sometimes referred to the order of Cetartiodactyla. The superorder of Euarchontoglires includes the orders Rodentia (mice, rats, porcupines, beavers, capybaras, and other gnawing mammals), Lagomorpha (rabbits and relatives), Scandentia (treeshrews), Dermoptera (colugos) and Primates (humans, apes and monkeys).

In one embodiment, the subject may be selected from humans, domestic mammals such as companion animals, working animals, livestock, and zoological/park mammals.

Preferably, the subject is a mammal, in particular a female mammal, more particularly a female mammal having developed lactiferous ducts such as a lactating female mammal.

These mammals include female humans, whose milk is needed for feeding their young, or expressed and donated to milk banks for redistribution to infants who may benefit from human milk for various reasons (e.g. premature neonates, babies with allergies, and metabolic diseases). The mammals also include female ungulates (even-toed and odd-toed) whose milk is used for commercial purposes, particularly as a food product for human consumption (e.g. cows, goats, sheep, yaks, water buffalos, horses, reindeer, camels, alpacas, bantengs, donkeys, oxen, zebu, moose and bison). The mammals may also include other lactating mammals which could benefit from the present invention such as those under veterinary care (e.g. domestic mammals including livestock, companion animals and working animals, or zoological/park mammals such as apes, monkeys, lions, zebras, and so on).

There are a number of causes for inflammation and/or infection in breast or udder tissue, more particularly in a mammary gland, which can occur in the subjects defined above. It may be caused by physical damage to breast or udder tissue such as by injury produced by physical force, chemicals introduced into the mammary gland or from bacteria and their toxins entering the breast or udder tissue.

Inflammation and/or infection in breast or udder tissue, more particularly in a mammary gland, are often associated with mastitis.

There are two types of mastitis: puerperal mastitis and non-puerperal mastitis. It is called puerperal mastitis when it occurs in lactating mothers, and non-puerperal otherwise. Mastitis can also occur in men, albeit rarely. Puerperal mastitis is the inflammation of the breast in connection with pregnancy, breastfeeding or weaning. Puerperal mastitis is thought to be caused by blocked milk ducts or milk excess. The incidence of puerperal mastitis is estimated to be in the range of 5-33% of breastfeeding mothers. The term non-puerperal mastitis describes inflammatory lesions of the breast occurring unrelated to pregnancy and breastfeeding. Non-puerperal mastitis may also be referred to as plasma cell mastitis, subareolar abscess, duct ectasia, periductal inflammation, Zuska's disease, and others.

Infections play only a minor role in the pathogenesis of human mastitis, with many cases of mastitis being aseptic under normal hygienic conditions. However, infection is a primary cause of mastitis in veterinary mastitis and in poorly hygienic conditions.

Where bacterial infection is involved, they are usually caused by a common bacterium found on the skin, inside the udder of animals, or on the skin of the teat. These bacteria are typically *Staphylococcus aureus* and *Streptococcus agalactiae*, but there are numerous others. The bacteria will usually enter breast or udder tissue through a break or crack in the skin. The infection then takes place in the tissue surrounding the milk ducts, causing swelling which compresses on the milk ducts, and pain in the infected breast.

Accordingly, the present invention provides a method for the treatment of inflammation and/or infection in breast or udder tissue comprising administering the composition or the formulation as defined above to a subject in need thereof. The present invention also provides use of a non-neutralised tocol phosphate and a vitamin A compound for the treatment of inflammation and/or infection in breast or udder tissue. The present invention further provides use of a non-neutralised tocol phosphate and a vitamin A compound in the manufacture of a medicament for the treatment of inflammation and/or infection in breast or udder tissue. The breast or udder tissue may be a mammary gland.

Generally, the term "treating" means affecting a subject, tissue or cell to obtain a desired pharmacological and/or physiological effect and includes: (a) inhibiting the inflammation and/or infection in breast or udder tissue, such as by arresting its development or further development; (b) relieving or ameliorating the effects of the inflammation and/or infection in breast or udder tissue, such as by causing regression of the effects of the inflammation and/or infection in breast or udder tissue; (c) reducing the incidence of the inflammation and/or infection in breast or udder tissue, or (d) preventing the inflammation and/or infection in breast or udder tissue from occurring in a subject, tissue or cell predisposed to the inflammation and/or infection in breast or udder tissue, or at risk thereof, but has not yet been diagnosed with a protective pharmacological and/or physiological effect so that the inflammation and/or infection in breast or udder tissue does not develop or occur in the subject, tissue or cell.

Although the present invention has been described with reference to treating inflammation and/or infection in breast or udder tissue, it will be appreciated that the present invention may also be useful in the treatment of other diseases or disorders associated with the inflammation and/or infection in breast or udder tissue such as, for example, inflammatory breast cancer, which has symptoms very similar to mastitis.

Reducing Somatic Cell Count

As mastitis occurs in domestic mammals as in humans, it is especially a concern in livestock, since milk from the affected udders of livestock may enter the food supply and pose a health risk. It is a major condition in some species, like dairy cows, because of the tremendous economic importance for the dairy industry. The same considerations apply to mastitis in sheep and goats and other milk producing livestock. It is also of economic importance in the sow, but, in this species, it is not related to public health. In other mammals, it is more an individual illness dealt with by veterinary practitioners.

There are several ways of classifying mastitis in domestic mammals. A simple classification recognises mastitis in two major groups: (a) contagious mastitis, which is caused by bacteria live on the skin of the teat and inside the udder and can be transmitted, for example, from one dairy cow to another during milking, and (b) environmental mastitis, which describes mastitis caused by organisms such as *Escherichia coli* which do not normally live on the skin or in the udder but which enter the teat canal when in contact with a contaminated environment. The percentage of cases of environmental mastitis is quite small compared to the total mastitis cases in domestic mammals.

Contagious mastitis can be divided into three groups: (i) clinical mastitis, (ii) sub-clinical mastitis, and (iii) chronic mastitis. Clinical mastitis is characterised by the presence of gross inflammation signs (swelling, heat, redness, pain). Three types of clinical mastitis exist. Peracute mastitis characterised by gross inflammation, disrupted functions (reduction in milk yield, changes in milk composition) and systemic signs (fever, depression, shivering, loss of appetite and loss of weight). Acute mastitis is similar to peracute mastitis, but with lesser systemic signs (fever and mild depression). Sub-acute mastitis when the mammary gland inflammation signs are minimal and no visible systemic signs. Sub-clinical mastitis is characterised by change in milk composition with no signs of gross inflammation or milk abnormalities. Changes in milk composition can be detected by special diagnostic tests. Chronic mastitis is where the inflammatory process exists for months, and may continue from one lactation period to another. Chronic mastitis for the most part exists as sub-clinical but may exhibit periodic flare-ups sub-acutely or acutely, which last for a short period of time.

Clinical and sub-clinical mastitis are the most important forms and can be diagnosed on the basis of bacteriological examination or by indirect tests, principally based on the somatic cell count, which is one of the indicators of the quality of milk. It should be noted that humans may also experience clinical and sub-clinical mastitis, however the milk of these subjects is usually not subjected to somatic cell count for diagnosis.

Somatic cells are leukocytes (white blood cells) and can contain lipolytic and proteolytic enzymes, which degrade fats and proteins, respectively. An increase in somatic cells count during a mastitis infection increases the amount of destructive enzymes present in the milk, which increases the rate of deterioration of the milk fat and protein. The number of somatic cells increases in response to pathogenic bacteria like *Staphylococcus aureus*, a cause of mastitis. The somatic cell count is usually quantified as cells per ml. With respect to dairy cows, it is generally considered that a somatic cell count less than 100,000 cells/ml is "uninfected", whereas a somatic cell count of greater than 100,000 cells/ml and up to 500,000 cells/ml is likely to be sub-clinical mastitis and a higher somatic cell count, that is greater than 500,000 cells/ml, is likely to be clinical mastitis.

The compositions and the formulations of the present invention have been shown to reduce the somatic cell count in livestock and therefore the compositions and the formulations of the present invention provide an effective treatment of mastitis, particularly clinical and sub-clinical mastitis.

Accordingly, the present invention also provides a method for reducing the somatic cell count in a lactating subject comprising administering the composition or the formulation as defined above to the lactating subject. The present invention also provides use of a non-neutralised tocol phosphate and a vitamin A compound for reducing the somatic cell count of a lactating subject. The present invention further provides use of a non-neutralised tocol phosphate and a vitamin A compound in the manufacture of a medicament for reducing the somatic cell count in a lactating subject.

In a preferred embodiment, the lactating subject is a female ungulate (even-toed and odd-toed), more particularly a female ungulate whose milk is used for commercial purposes including cows, goats, sheep, pigs, yaks, water buffalo, horses, reindeer, camels, alpacas, bantengs, donkeys, oxen, zebu, moose and bison. The lactating subject may also be a lactating human.

Administration of the composition or the formulation to the lactating subject may reduce the somatic cell count by up to 90%, up to 80%, up to 70%, up to 60%, up to 50%, up to 40%, up to 30%, up to 20%, or up to 10%. The reduction may be achieved in 1 week, 2 weeks, 3 weeks, 4 weeks, 5 weeks, or more, with daily or weekly administration of an effective dose of the composition or the formulation to the lactating subject.

Vitamin E Supplementation

A composition or a formulation of the present invention may also supplement vitamin E levels (µmol/L) in a subject. Accordingly, the present invention also provides a method for supplementing vitamin E levels in a subject comprising administering the composition or the formulation as defined above to the subject. The present invention also provides use of a non-neutralised tocol phosphate and a vitamin A compound for supplementing vitamin E levels in a subject. The present invention further provides use of a non-neutralised tocol phosphate and a vitamin A compound in the manufacture of a medicament to supplement vitamin E levels in a subject.

Administration Route

Routes of administration can broadly be divided into a three categories by effect, namely, "topical" where the desired effect is local, so the substance is applied directly where its action is desired, "enteral" where the desired effect is systemic (non-local) so the substance is given via the digestive tract, and "parenteral" where the desired effect is systemic, so the substance is given by routes other than the digestive tract.

The formulation of the present invention is suitable for topical, enteral or parenteral administration.

Examples of topical routes of administration having a local effect include epicutaneous (onto the skin) including the skin of the breast of a human subject or the udder of an animal subject.

Examples of enteral routes of administration having a systemic (non-local) effect include any form of administration that involves any part of the gastrointestinal tract, such as oral (into the mouth), intranasal (into the nose), rectal (into the rectum), and vaginal (into the vagina). Oral administration includes buccal administration (absorbed through the cheek near the gumline), and sublingual administration (under the tongue).

Examples of parenteral routes of administration by injection, infusion or diffusion having a systemic effect include intravenous (into a vein), intraarterial (into an artery), intramuscular (into a muscle), intracardiac (into the heart), subcutaneous (under the skin), percutaneous (via needle-puncture into the skin), intradermal (into the skin itself), intrathecal (into the spinal canal), intraperitoneal (infusion or injection into the peritoneum), intravesical infusion (infusion into the urinary bladder), epidural (injection or infusion into the epidural space), transdermal or transcutaneous (diffusion through the intact skin), transmucosal (diffusion through a mucous membrane), insufflation (diffusion through the nose), inhalational (diffusion through the mouth), and intramammary (into mammary tissue).

Topical, in particular epicutaneus, enteral, in particular oral, and parental, in particular intramammary, routes of administration are preferred.

Dosage Form

The compositions and the formulations of the present invention may be prepared into any suitable dosage form for topical, enteral, parenteral administration.

A person skilled in the art would readily appreciate what would be a suitable dosage form for topical, enteral, parenteral administration Suitable dosage forms for topical administration include creams, lotions, gels and the like. The dosage form may also be a patch or other device. As one example for veterinary applications, the device could be in the form of a cover for the teat such as a Teatseal®, which is placed onto the teat after milking as a barrier to bacterial contamination. In this application, the composition or the formulation of the present invention could be provided on the inner surface of such a teat cover so that the composition or the formulation contacts the teat when in place.

Suitable dosage forms for enteral administration would include but not be limited to capsules, tablets, pills, or specialty tablets such as buccal, sublingual, chewable tablets or orally-disintegrating tablets. Another example of a suitable dosage form would be edible thin films.

Other suitable dosage forms for enteral administration include liquid solutions or suspensions. Suitable liquid solution or suspension dosage forms may be in the form of a drink, such as sports drinks containing electrolytes (e.g. gatorade), or syrup and elixirs. Other suitable liquid solution or suspension dosage forms include nasal delivery solutions and oral suspensions including liquid solutions or suspensions. For veterinary purposes, the liquid solution or suspension may be in the form of a "drench". The liquid solution or suspension may also be used in the preparation of an edible product, such as a biscuit or cake, suitable for human or animal consumption. A product for animal consumption may also include appropriate animal feeds.

The dosage form for enteral administration may also be a powder or solid crystal, which can be either dissolved or suspended in a liquid before administration. Alternatively, the powder may be consumed directly or added to a food or drink product for consumption. In the case of farm animals, the formulation may be added directly to the animal feed.

Where the composition or the formulation has a disagreeable taste, additives with sufficient flavour to disguise the bad taste may be added to the dosage form (e.g. masking agents).

Examples of suitable dosage forms for parenteral administration include but are not limited to injectables (i.e. solutions, suspensions, emulsions, and dry powders for reconstitution), intramammary infusions, intravaginal delivery systems, and implants.

Dosage Regime

The term "therapeutically effective amount" refers to the amount of a composition or a formulation of the present invention that will elicit the biological or medical response of a subject, tissue or cell that is being sought by the researcher, veterinarian, medical doctor or other clinician. Administration of a "therapeutically effective amount" of the composition or the formulation of the present invention should obtain a desired pharmacological and/or physiological effect and includes: (a) inhibiting the inflammation and/or infection in breast or udder tissue, such as by arresting its development or further development; (b) relieving or ameliorating the effects of the inflammation and/or infection in breast or udder tissue, such as by causing regression of the effects of the inflammation and/or infection in breast or udder tissue; (c) reducing the incidence of the inflammation and/or infection in breast or udder tissue, or (d) preventing the inflammation and/or infection in breast or udder tissue from occurring in a subject, tissue or cell predisposed to the inflammation and/or infection in breast or udder tissue, or at risk thereof, but has not yet been diagnosed with a protective pharmacological and/or physiological effect so that the inflammation and/or infection in breast or udder tissue does not develop or occur.

It will be understood that the specific dose level and frequency of dosage for any particular subject may be varied and will depend upon a variety of factors including the activity of the composition or formulation employed, and the metabolic stability and length of action of that composition or the formulation; the age, body weight, general health, sex, or diet of the subject; the route of administration used; the mode and time of administration of the composition or the formulation; the rate of excretion or clearance of the composition or the formulation from the body; the non-neutralised tocol phosphate and the vitamin A compound used in the composition or the formulation; the severity of the inflammation or infection of the breast or udder tissue of the subject; and the particular subject undergoing treatment.

Suitable intervals of dosing include monthly, every two months or longer, biweekly, weekly, daily, or multiple times per day. Preferably, the composition or the formulation of the present invention is administered weekly, daily, or multiple times per day.

The composition or the formulation will generally contain an appropriate dosage level of non-neutralised tocol phosphate, which may be about 0.1 to about 20 mg per kg subject body weight per day which can be administered in single or multiple doses. Preferably, the dosage level will be about 0.1 to about 15 mg/kg per day; about 0.1 to about 10 mg/kg per day; more preferably, about 0.1 to about 10 mg/kg per day, about 0.1 to about 5 mg/kg per day, about 0.1 to about 2.5 mg/kg per day or about 0.1 to about 2 mg/kg per day. A suitable dosage level may be about 0.1 to about 7.5 mg/kg per day. For example, within the above dosage ranges, the dosage may be about 0.1 mg/kg per day, about 0.2 mg/kg per day, about 0.4 mg/kg per day, about 0.6 mg/kg per day, about 0.7 mg/kg per day, about 0.8 mg/kg per day, about 0.9 mg/kg per day, about 1 mg/kg per day, about 1.2 mg/kg per day, about 1.4 mg/kg per day, about 1.5 mg/kg per day, about 1.6 mg/kg per day, about 1.7 mg/kg per day, about 1.8 mg/kg per day, about 1.9 mg/kg per day, about 2 mg/kg per day, about 2.2 mg/kg per day, about 2.5 mg/kg per day, about 3 mg/kg per day, about 5 mg/kg per day, about 7.5 mg/kg per day, or about 10 mg/kg per day.

The composition or the formulation will generally contain an appropriate dosage level of the vitamin A compound, which may be about 10 to about 1000 µg per kg subject body weight per day which can be administered in single or multiple doses. Preferably, the dosage level will be about 10 to about 850 µg/kg per day; about 10 to about 800 µg/kg per day; about 10 to about 500 µg/kg per day; or less than about 300 µg/kg per day. More preferably, the dosage level will be about 10 to about 500 µg/kg per day, 10 to about 275 µg/kg per day, 10 to about 250 µg/kg per day, 20 to about 250 µg/kg per day, 25 to about 250 µg/kg per day, 10 to about 200 µg/kg per day or 50 to about 200 µg/kg per day. A suitable dosage level may be about 10 to about 300 µg/kg per day. For example, within the above dosage ranges, the dosage may be about 10 µg/kg per day, about 20 µg/kg per day, about 40 µg/kg per day, about 50 µg/kg per day, about 60 µg/kg per day, about 70 µg/kg per day, about 75 µg/kg per day, about 80 µg/kg per day, about 85 µg/kg per day, about 90 µg/kg per day, about 95 µg/kg per day, about 100 µg/kg per day, about 125 µg/kg per day, about 150 µg/kg per day, about 155 µg/kg per day, about 160 µg/kg per day, about 165 µg/kg per day, about 170 µg/kg per day, about 175 µg/kg per day, about 180 µg/kg per day, about 190 µg/kg per day, about 200 µg/kg per day, about 225 µg/kg per day, about 250 µg/kg per day, about 300 µg/kg per day, about 400 µg/kg per day, or about 500 µg/kg per day.

In one embodiment, the composition or the formulation, will be administered daily and will comprise a tocol phosphate in an amount of about 0.1 to about 15 mg/kg, and a vitamin A compound in an amount of about 10 to about 500 µg/kg. In cases of sub-clinical mastitis, the subject may be administered a daily dose of the composition or the formulation comprising a non-neutralised tocol phosphate in an amount of about 0.1 to about 1.5 mg/kg and a vitamin A compound in an amount of about 10 to about 150 µg/kg. In the cases of clinical mastitis, the subject may be administered a daily dose of the composition or the formulation with increased amounts of a non-neutralised tocol phosphate and a vitamin A compound. For example, the composition or the formulation may comprise a non-neutralised tocol phosphate in an amount of about 1.0 to about 5.0 mg/kg and a vitamin A compound in an amount of about 100 to about 300 µg/kg.

In one embodiment, an effective dosage form comprises non-neutralised TPM and a vitamin A compound such as beta-carotene in any of the above defined amounts.

FIGURES

The invention is described further by way of example with reference to the accompanying drawings in which.

EXAMPLES

Figure 1A:
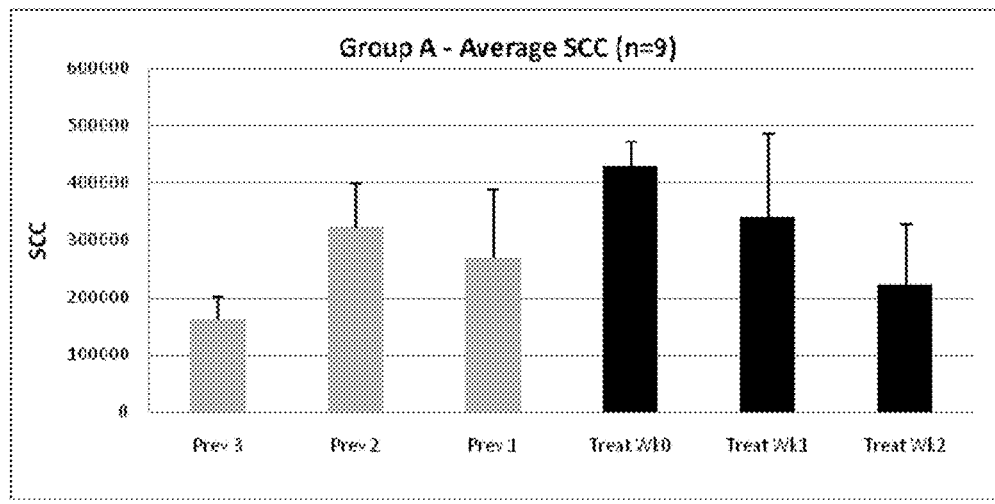
FIG. 1A is a bar chart showing the average somatic cell count of the dairy cows of Group A over a period of time prior to treatment with Formulation A (represented in grey) and over a 2 week treatment period (represented in black).
Figure 1B:
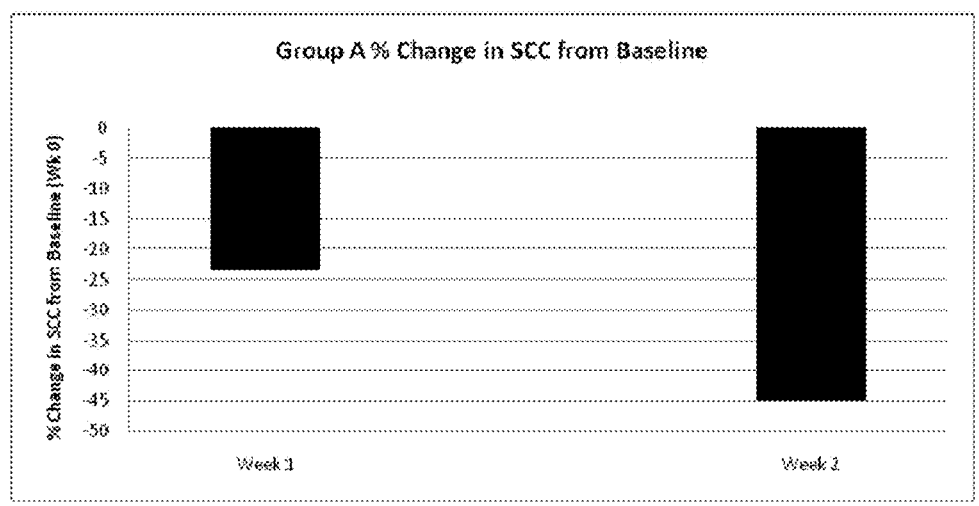
FIG. 1B is a bar chart showing the percentage change in the average somatic cell count of the dairy cows of Group A over a period prior to treatment with Formulation A and over a 2 week treatment period.

The invention is described further by reference to the following non-limiting examples of the invention.

Example 1: Preparation of Formulations

The following formulations of the present invention were prepared for oral delivery.

| Component | Formulation A | Formulation B |
| --- | --- | --- |
| Non-neutralised TPM | 1% w/w (~0.5 g) | 2% w/w (~1 g) |
| Beta-carotene | 0.1% w/w (~50 mg) | 0.2% w/w (~100 mg) |
| Olive oil | balance to 100% (total ~60 ml) | balance to 100% (total ~60 ml) |

Each of Formulations A and B were prepared by combining non-neutralised TPM (pH about 2 to about 4) with olive oil, and stirring the mixture at about 70° C. The mixture was then cooled to below 40° C. before the beta-carotene was added, with stirring.

Example 2: Treatment of Dairy Cows Suffering Mastitis 35 dairy cows showing signs of either sub-clinical or clinical mastitis with persistent elevated somatic cell counts, were kept separated from the main herd (consisting of approximately 300 head). Various attempts to treat the mastitis in the cattle had been made, and the mastitis was considered problematic.

18 of the 35 dairy cows were selected based on their somatic cell counts; their somatic cell counts and previous antibiotic treatment was documented. The 18 dairy cows were divided into 2 groups consisting of 9 dairy cows each and designated Group A and Group B.

Final antibiotic treatment ceased at least 4 weeks prior to commencing treatment with formulations of the present invention. A baseline or treatment week 0 somatic cell count was measured.

At treatment week 0, the Group A dairy cows had elevated somatic cell counts but not severe, with an average somatic cell count of 429,000 cells/ml, whereas the Group B dairy cows showed some clinical signs of mastitis and generally had much higher somatic cell counts with an average somatic cell count of 1,243,222 cells/ml.

The Group A dairy cows were treated with Formulation A of Example 1 and the Group B dairy cows were treated with Formulation B of Example 1.

Both groups were treated daily using an oral drench, administered each morning after milking. The oral drench was delivered via a drenching gun that delivered approximately 60 ml of the relevant formulation.

Each week, a milk sample was collected from each of the dairy cows in the respective groups and somatic cell counts were measured for each individual dairy cow.

Group A Results

The Group A dairy cows were treated for 2 weeks. The results of this study are shown in the table below.

TABLE 1

Somatic cell counts for the Group A dairy cows

| Time point | Average somatic cell count (cells/ml) | Average percentage change in somatic cell count |
|---|---|---|
| Previous 6 (reading taken 33 weeks before Treatment Week 0) | 311,000 | |
| Previous 5 (reading taken 28 weeks before Treatment Week 0) | 128,400 | |
| Previous 4 (reading taken 23 weeks before Treatment Week 0) | 222,000 | |
| Previous 3 (reading taken 17 weeks before Treatment Week 0) | 161,000 | |
| Previous 2 (reading taken 12 weeks before Treatment Week 0) | 322,444 | |
| Previous 1 (reading taken 7 weeks before Treatment Week 0) | 271,000 | |
| Treatment Week 0 | 429,000 | |
| Treatment Week 1 | 341556 | −23% |
| Treatment Week 2 | 222,111 | −45% |

The results shown for the somatic cell counts are an average of the somatic cell counts of the 9 dairy cows for this group. The percentage change values were calculated as the difference in the somatic cell count compared to the somatic cell count at treatment week 0, and expressed as a percentage of the somatic cell count for that treatment week.

The graph shown in FIG. 1A shows the decrease in somatic cell count over the treatment period. After 2 weeks of daily treatment, the average somatic cell count decreased from 429,000 cells/ml to 222,111 cells/ml, which correlates to a 45% reduction in the somatic cell count after 2 weeks of treatment.

Group B Results

The Group B dairy cows were treated for 5 weeks. The results of this study are shown in the table below.

TABLE 2

Somatic cell counts for the Group B dairy cows

| Time point | Average somatic cell count (cells/ml) | Average percentage change in somatic cell count |
|---|---|---|
| Previous 6 (reading taken 33 weeks before Treatment Week 0) | 1,491,000 | |
| Previous 5 (reading taken 28 weeks before Treatment Week 0) | 604,857 | |
| Previous 4 (reading taken 23 weeks before Treatment Week 0) | 221,375 | |
| Previous 3 (reading taken 17 weeks before Treatment Week 0) | 234,000 | |
| Previous 2 (reading taken 12 weeks before Treatment Week 0) | 560,111 | |
| Previous 1 (reading taken 7 weeks before Treatment Week 0) | 1,122,667 | |
| Treatment Week 0 | 1,243,222 | |
| Treatment Week 1 | 2,247,333 | 109% |
| Treatment Week 2 | 1,145,444 | 12% |
| Treatment Week 3 | 1,265,556 | 7% |
| Treatment Week 4 | 852,625 | −33% |
| Treatment Week 5 | 516,556 | −54% |

The results shown for the somatic cell counts are an average of the somatic cell counts of the 9 dairy cows for this group. The percentage change values were calculated as the difference in the somatic cell count compared to the somatic cell count at treatment week 0, and expressed as a percentage of the somatic cell count for that treatment week.

Figure 2A:
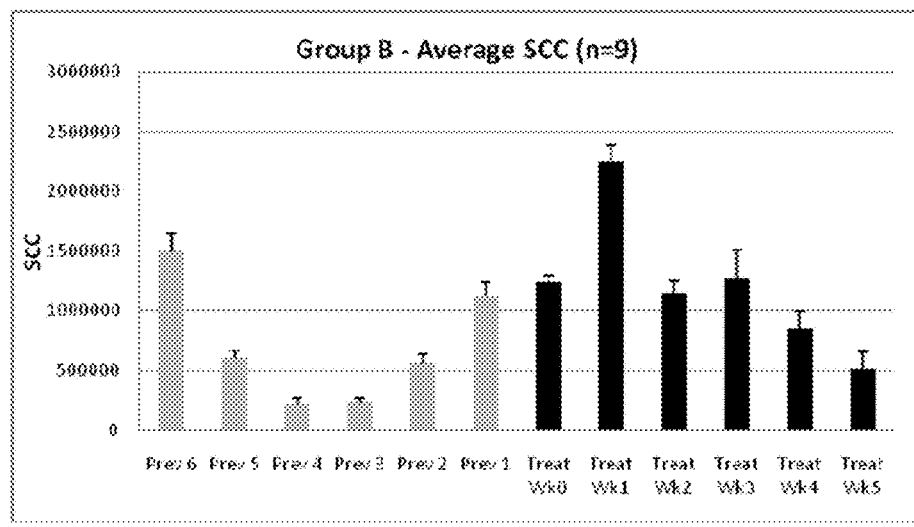
FIG. 2A is a bar chart showing the average somatic cell count of the dairy cows of Group B over a period of time prior to treatment with Formulation B (represented in grey) and over a 5 week treatment period (represented in black).
Figure 2B:
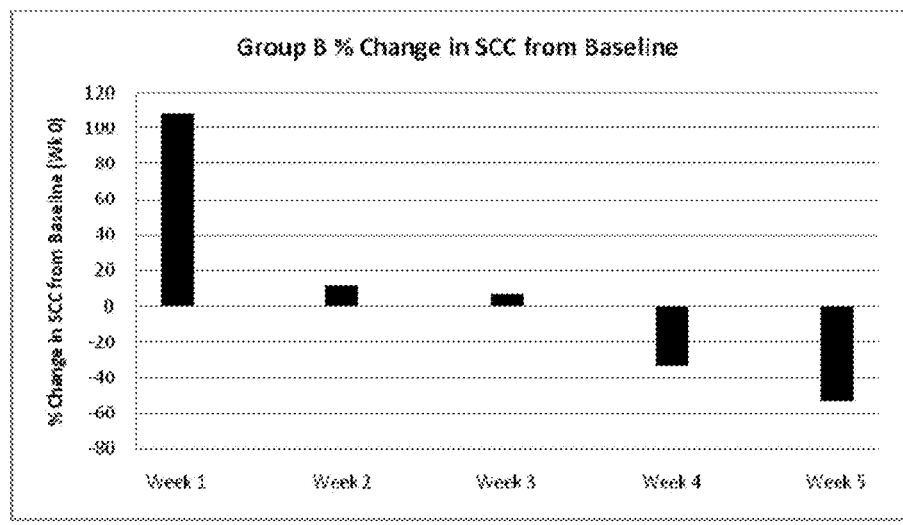
FIG. 2B is a bar chart showing the percentage change in the average somatic cell count of the dairy cows of Group B over a period of time prior to treatment with Formulation B and over a 5 week treatment period.

The graph shown in FIG. 2A shows the decrease in somatic cell count over the treatment period. After 5 weeks of daily treatment, the average somatic cell count decreased from 1,243,222 cells/ml to 516,556 cells/ml, which correlates to a 54% reduction in the somatic cell count after 5 weeks of treatment.

This example clearly demonstrates the effectiveness of formulations of the present invention in the reduction of somatic cell count and therefore treatment of mastitis in dairy cows.

Example 3: Vitamin E Supplementation in Dairy Cows Suffering Mastitis

The following are results of vitamin E levels in 4 dairy cows showing signs of mastitis treated with a formulation of the present invention after 1 week. The blood of the 4 dairy cows was tested at a commercial pathology laboratory.

| | Baseline Vitamin E (µmol/L) | Supplementation Vitamin E (µmol/L) | Change | % Change |
|---|---|---|---|---|
| DC1 | 13.6 | 13.9 | +0.3 | +2.2 |
| DC2 | 9.6 | 10.8 | +1.2 | +12.5 |
| DC3 | 14.6 | 15.2 | +0.6 | +4.1 |
| DC4 | 16.1 | 16.7 | +0.6 | +3.7 |

Example 4: Formulations Comprising Nutrients

Further embodiments of an oral drench can be prepared according to Example 1, but comprising additional nutrients, such as for example, selenium, copper, zinc, a vitamin E compound. The nutrients are added at the same time as the beta-carotene.

Specifically designed oral drenches would be administered to dairy cattle as described in Example 2, and compared with dairy cattle administered with an oral drench not comprising any nutrients. The blood levels of vitamin E could also be measured as in Example 3.

Example 5: Optimisation of Administration Route

Formulations as described in Example 4 could also be prepared using suitable excipients as intramammary infusions or topical creams. These could be compared against the effect of the drench formulation as outlined in Examples 2, 3 and/or 4.

Many modifications may be made to the embodiments and examples described above without departing from the spirit and scope of the invention.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for reducing somatic cell count in a lactating subject comprising administering a formulation to the lactating subject, wherein the formulation comprises a non-neutralised tocol phosphate, a vitamin A compound, and a hydrophobic delivery vehicle,
wherein the non-neutralised tocol phosphate is a combination of a non-neutralised mono-(tocopheryl) phosphate and a non-neutralised di-(tocopheryl) phosphate.

2. A method for treating inflammation and/or infection in breast or udder tissue comprising administering a formulation to a subject in need thereof, wherein the formulation comprises a non-neutralised tocol phosphate, a vitamin A compound, and a hydrophobic delivery vehicle,
wherein the non-neutralised tocol phosphate is a combination of a non-neutralised mono-(tocopheryl) phosphate and a non-neutralised di-(tocopheryl) phosphate.

3. The method of claim 2 wherein the breast or udder tissue is a mammary gland.

4. The method of claim 2 wherein the inflammation and/or infection is mastitis.

5. The method of claim 2 wherein the subject is selected from humans, domestic mammals including companion animals, working animals, livestock, and zoological/park mammals.

6. The method of claim 2 wherein the combination of the non-neutralised mono-(tocopheryl) phosphate and the non-neutralised di-(tocopheryl) phosphate comprises: (a) a compound selected from the group consisting of non-neutralised mono-(tocopheryl) phosphate, non-neutralised mono-(tocopheryl) phosphate monosodium salt, non-neutralised mono-(tocopheryl) phosphate disodium salt, non-neutralised mono-(tocopheryl) phosphate monopotassium salt, non-neutralised mono-(tocopheryl) phosphate dipotassium salt, or a combination of any thereof; and (b) a compound selected from the group consisting of non-neutralised di-(tocopheryl) phosphate, non-neutralised di-(tocopheryl) phosphate monosodium salt, and non-neutralised di-(tocopheryl) phosphate monopotassium salt, or a combination of any thereof.

7. The method of claim 2 wherein the ratio (w/w %) of non-neutralised mono-(tocopheryl) phosphate to non-neutralised di-(tocopheryl) phosphate is about 4:1 to about 1:4.

8. The method of claim 2 wherein the non-neutralised tocol phosphate has a pH of less than about 4.

9. The method of claim 2 wherein the non-neutralised tocol phosphate comprises from about 0.01% w/w up to about 40% w/w of the total concentration of the composition.

10. The method of claim 2 wherein the vitamin A compound is selected from the group consisting of vitamin A, a derivative of vitamin A, a metabolite of vitamin A, a precursor of vitamin A, or pro-vitamin A, or a combination thereof.

11. The method of claim 2 wherein the vitamin A compound is a carotenoid.

12. The method of claim 11 wherein the carotenoid is selected from the carotene class including alpha-carotene, beta-carotene, gamma-carotene, beta-cryptoxanthin and lycopene.

13. The method of claim 2 wherein the ratio (w/w %) of non-neutralised tocol phosphate to vitamin A compound is from about 0.01:1 to about 100:1.

14. The method of claim 2 wherein the vitamin A compound is beta-carotene.

15. The method of claim 2 wherein the formulation further comprises a nutrient compound selected from the group consisting of antioxidants, vitamins, minerals and trace elements.

16. The method of claim 15 wherein the nutrient compound is selected from the group consisting of coenzyme Q10, ubiquinol, vitamin D compounds, vitamin E compounds, vitamin K compounds, folic acid, vitamin B compounds, vitamin C, vitamin P, vitamin F, lutein, zeaxanthin, cysteine, flavonoids, isoflavones, bilberry, *ginkgo biloba*, grape seed extract, phytonutrients, alpha lipoic acid, bilberry, bioflavinoids, unsaturated fatty acids, calcium, phosphorus, magnesium, fluorine, phosphorus, sulfur, sodium, potassium, chloride, calcium, iodine, cobalt, copper, iron, manganese, molybdenum, selenium, zinc, chromium, cadmium, fluorine, nickel, silicon, tin, vanadium, niacin, and combinations thereof.

17. The method of claim 2 wherein the hydrophobic delivery vehicle is an oil or a wax.

18. The method of claim 2 wherein the hydrophobic delivery vehicle is present in an amount of at least about 60.0% w/w of the total concentration of the formulation.

19. The method of claim 2 wherein the non-neutralised tocol phosphate has a pH of about 2 to about 4.

* * * * *